United States Patent
Tingley

(10) Patent No.: US 6,597,997 B2
(45) Date of Patent: *Jul. 22, 2003

(54) NON-INVASIVE PIPE INSPECTION SYSTEM

(75) Inventor: Robert Tingley, Ashland, MA (US)

(73) Assignee: The Charles Stark Draper Laboratory, Inc., Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/920,379

(22) Filed: Aug. 1, 2001

(65) Prior Publication Data

US 2002/0035437 A1 Mar. 21, 2002

Related U.S. Application Data

(63) Continuation-in-part of application No. 09/655,954, filed on Sep. 6, 2000.
(60) Provisional application No. 60/222,170, filed on Aug. 1, 2000.

(51) Int. Cl.[7] .................................................. G01R 29/00
(52) U.S. Cl. ........................ 702/34; 702/33; 324/635; 73/760; 73/801
(58) Field of Search ................... 702/34, 33; 73/584, 73/596, 632, 579, 592, 602, 622, 628, 801, 627, 629, 760; 324/220, 637, 534, 642, 635, 639, 644

(56) References Cited

U.S. PATENT DOCUMENTS

| | | | | |
|---|---|---|---|---|
| 3,634,753 A | * | 1/1972 | Unterberger | 180/313 |
| 3,950,695 A | | 4/1976 | Barringer | 324/3 |
| 3,974,680 A | | 8/1976 | Beaver | 73/40.5 |
| 3,978,396 A | | 8/1976 | Inouye et al. | 324/6 |
| 4,092,868 A | | 6/1978 | Thompson et al. | 73/638 |

(List continued on next page.)

FOREIGN PATENT DOCUMENTS

| | | | | |
|---|---|---|---|---|
| JP | 181146 A | 7/1995 | | G01N/22/00 |
| JP | 123108 A | 5/1998 | | G01N/29/20 |
| WO | 46545 A | 8/2000 | | F17D/3/01 |

OTHER PUBLICATIONS

Cheo et al., "Detection Of Voids And Contaminants In Polyethylene Insulated Cable Utilizing A Fir Laser Beam", IEEE Transactions Power Apparatus and Systems, vol. PAS–102, No. 3, Mar. 1983, pp. 521–526.

Gauthier et al., "EMAT Generation Of Horizontally Polarized Guided Shear Waves For Ultrasonic Pipe Inspection", International Pipeline Conference—vol. 1, 1998, pp. 327–334.

Rose et al., "Ultrasonic Guided Wave Inspection Concepts For Steam Generator Tubing", Materials Evaluation, vol. 52, No. 2, Feb. 1994, pp. 307–311.

George A. Alers, "Application Of Special Wave Modes To Industrial Inspection Problems", 1994 International Mechanical Engineering Congress and Exposition—AMD–vol. 188, Nov. 1994, pp. 1–9.

(List continued on next page.)

Primary Examiner—John Barlow
Assistant Examiner—Hien Vo
(74) Attorney, Agent, or Firm—Testa, Hurwitz & Thibeault, LLP

(57) ABSTRACT

The invention is directed to a system and method for non-invasive pipe inspection. According to one embodiment, the system includes a processor, an analyzer, and a wave launcher. The wave launcher is adapted to transmit an input wideband waveform having a selected input energy into the pipe along a longitudinal axis, and to receive from the pipe a reflected component of the input waveform having a reflected energy. The analyzer is adapted to generate the input waveform, and to receive the reflected component of the input waveform from the wave launcher. The processor is adapted to compare the input waveform with the reflected component of the input waveform to determine characteristics.

28 Claims, 22 Drawing Sheets

U.S. PATENT DOCUMENTS

| | | | |
|---|---|---|---|
| 4,161,687 A | 7/1979 | Lytle et al. | 324/6 |
| 4,603,584 A | 8/1986 | Bartle et al. | 73/599 |
| 5,155,439 A | 10/1992 | Holmbo et al. | 324/534 |
| 5,303,079 A * | 4/1994 | Gnauck et al. | 359/180 |
| 5,392,652 A * | 2/1995 | Levesque et al. | 73/629 |
| 5,455,516 A * | 10/1995 | Jean et al. | 324/636 |
| 5,500,730 A | 3/1996 | Johnson | 356/73.1 |
| 5,612,625 A | 3/1997 | Suyama et al. | 324/635 |
| 5,719,503 A | 2/1998 | Burnett | 324/534 |
| 5,864,232 A | 1/1999 | Laursen | 324/220 |
| 5,987,990 A | 11/1999 | Worthington et al. | 73/592 |
| 5,990,689 A | 11/1999 | Poncon | 324/627 |
| 6,307,191 B1 | 10/2001 | Waycuilis | 219/687 |

OTHER PUBLICATIONS

Alleyne et al., "The Effect Of Discontinuities On The Long–Range Propagation Of Lamb Waves In Pipes", Institution of Mechanical Engineers, Part E: Journal of Process Mechanical Engineering, vol. 210, No. E3, 1996, pp. 217–226.

Michael Lowe, "Characteristics Of The Reflection Of Lamb Waves From Defects In Plates And Pipes", Review of Progress in Quantitative Nondestructive Evaluation, vol. 17A, 1998, pp. 113–120

Cawley et al., "The Use Of Lamb For The Long Range Inspection Of Large Structures", Ultrasonics, vol. 34, No. 2–5, Jun. 1996, pp. 287–290.

Lowe et al., "Defect Detection In Pipes Using Guided Waves", Ultrasonics, vol. 36, No. 1–5, Feb. 1998, pp. 147–154.

PCT International Search Report for International Application No.: PCT/US01/24083, mailed on Jun. 7, 2002.

* cited by examiner

NON-INVASIVE PIPE INSPECTION SYSTEM

REFERENCE TO RELATED APPLICATION

This application claims priority to and is a continuation-in-part of U.S. patent application Ser. No. 09/655,954, entitled "Non-Invasive Pipeline Inspection System," filed on Sep. 6, 2000, which itself claims priority to Provisional U.S. patent application Ser. No. 60/222,170, entitled "Non-Invasive Pipeline Inspection Using Radiosounding," filed on Aug. 1, 2000. These co-pending applications are hereby incorporated by reference.

FIELD OF THE INVENTION

This invention relates generally to inspecting a pipe for anomalies, and more specifically to inspecting a pipe using a reflected component of an input waveform.

BACKGROUND OF THE INVENTION

To maintain substantial fluid flow through a pipe, internal pipe characteristics need to be monitored so that defects, obstructions, and other anomalies in the pipe can be detected and repaired efficiently, or in the case of quality assurance testing, discarded. In addition to manufacturing defects and other anomalies, such as obstructions, affecting fluid flow in the pipe, the pipe may bend and/or buckle in response to changes in pressure, such as result when pipes are laid underwater. Frequently, companies must endure substantial monetary costs and schedule delays due to the detection and repair of these pipe anomalies.

In some conventional pipe inspection systems, an internal, invasive device crawls the length of the pipe to inspect it for anomalies. This device, typically referred to as a "pig", poses a serious blockage to the normal fluid flow through a pipe. A pig also may require several days for the inspection of a lengthy pipe. Furthermore, the amount of data a pig can record, the life of its battery, and the wear of its components from crawling the pipe all limit the usefulness of the pig.

Measuring the acoustic signature of a pipe is another technique used to detect pipe anomalies. This technique sometimes involves hitting the pipe on its side with a hard object, such as a hammer, and then measuring the acoustic signature of the pipe. Anomalies often alter the acoustic signature of a pipe as compared to a pipe with no such anomalies. However, the magnitude of the anomaly that may be detected is dependent upon the wavelength of the waveform transmitted along the pipe, and sound waves generally have longer wavelengths than some other waveforms. Therefore, this technique typically fails to detect smaller-sized anomalies in a pipe and is relatively ineffective in pre-installation quality assurance testing.

Pulse propagation may also be used to detect pipe anomalies. According to one technique, two pulses are transmitted along the pipe from opposing locations towards an intersecting location. The pulses intersect and are each modified by collision with the oppositely directed pulse. A receiver is positioned at the intersecting location and, after receiving the modified pulses, analyzes at least one indicator characteristic of one of the modified pulses to determine whether an anomaly exists between the receiver and the corresponding transmitter. However, this technique usually requires two separate transmitters and a separate receiver, each of which increases the costs associated with detecting anomalies. Also, pulse propagation analysis may further require inserting the receiver into a location in the pipe not normally open for device placement.

Another conventional approach is an ultrasonic guided wave inspection technique that uses stress waves, such as Lamb waves. Since Lamb waves are typically guided along the pipe, lateral spreading of the energy associated with these waves does not usually occur and the propagation is essentially one-dimensional. For this reason, Lamb waves normally propagate over longer distances than other types of waves, such as bulk waves. Unfortunately, at least two modes typically exist at any frequency for Lamb waves. Furthermore, the modes are generally dispersive, which means that the shape of the propagating waveform varies with distance along the pipe. Consequently, the signals typically suffer from signal-to-noise problems and are difficult to interpret.

Accordingly, it is desirable to produce a system that is capable of detecting an internal characteristic of a pipe in a non-invasive fashion. It is also desirable to be able to inspect a pipe faster than currently possible, as well as to be able to accurately detect smaller-sized anomalies in a pipe. It is further desirable to provide improved quality assurance testing prior to pipe installation.

SUMMARY OF THE INVENTION

Briefly, the invention relates to a system and method for inspecting a pipe. In one embodiment, the invention provides a system for detecting and characterizing an anomaly in a pipe. In another embodiment, the invention provides a system that can also determine the longitudinal path/shape of the pipe. With a starting point and the longitudinal shape of the pipe, a further embodiment of the invention can also determine the location of a pipe buried underground or even underwater.

According to one preferred embodiment, the system includes a processor, an analyzer, and a wave launcher. In an alternate embodiment, the analyzer, wave launcher, and processor are incorporated into a single unit, thereby eliminating the external connections between the devices. In yet another embodiment, an integrated analyzer and an integrated wave launcher are located inside an end portion of the pipe to be inspected. The wave launcher communicates with the pipe, and is adapted to transmit an input waveform having a selected input energy along a longitudinal axis of the pipe. Examples of the type of input waveform include, but are not limited to, an electromagnetic waveform, a wideband waveform, and an acoustic waveform. Further examples of input wideband waveforms include, but are not limited to, a chirp waveform, a spread spectrum waveform, a wavelet waveform, and a solitons waveform. The wave launcher is further adapted to receive a reflected component of the input waveform having a characteristic reflected energy. An example of the wave launcher includes an antenna adapted to transmit the input waveform along a longitudinal pipe.

In one embodiment, the wave launcher transmits an input waveform having a selected cutoff frequency. The cutoff frequency is a frequency below which no input waveform propagates. This cutoff frequency is the minimum frequency needed to propagate the first mode of the input waveform along the longitudinal axis of pipe.

The invention can also be used to inspect a pipe prior to laying the pipe. This inspection is typically used as a quality control measurement. For example, the operator can inspect the pipe for a manufacturing defect, an anomaly that arose during transportation of the pipe, such as a rock, or for an anomaly that arose due to the age of the pipe, such as rust. Furthermore, the processor of the inspection system can display details to particular manufacturing tolerances that the pipe fails to meet.

In a further embodiment, the processor of the inspection system is adapted to determine an axial curvature of the pipe as the pipe is being laid. Moreover, the determination can be repeated multiple times to enable the processor to provide a substantially real-time measurement of curves in the pipe. In one embodiment, the inspection system displays a graphical representation of the substantially real-time measurement of the pipe curvature, along with information regarding resultant mechanical stresses on the pipe to an operator. The operator can use such information, for example, to guide a pipe installation process to avoid potentially damaging mechanical stresses being inflicted on the pipe.

In a further embodiment, the pipe inspection system is adapted to transmit a microwave waveform into pipe to dissolve an anomaly. In a related embodiment, the pipe is coated with a microwave sensitive coating and/or wrap that is adapted to heat in response to the microwave waveform.

In another embodiment, the pipe inspection system includes a wave launcher, an analyzer, a clamp, and an umbilical. The wave launcher is adapted to transmit an input waveform having a selected input energy along a longitudinal axis of a first section of pipe. The wave launcher is also able to receive a reflected portion of the input waveform from the pipe. The analyzer communicates with the wave launcher and is adapted to generate the input waveform and to receive the reflected portion of the waveform from the wave launcher. The clamp mechanically connects with the analyzer and temporarily connects the first section of the pipe with the second section of the pipe. An operator uses the umbilical to move the wave launcher and/or the analyzer from the first section of the pipe to the second section of the pipe to enable the wave launcher to transmit the input waveform along the longitudinal axis of the first section of the pipe and the second section of the pipe.

BRIEF DESCRIPTION OF THE DRAWINGS

Advantages of the invention will become better understood by referring to the following drawings, which show a system according to an illustrative embodiment of the invention and in which.

DESCRIPTION OF THE ILLUSTRATIVE EMBODIMENTS

Figure 1A:
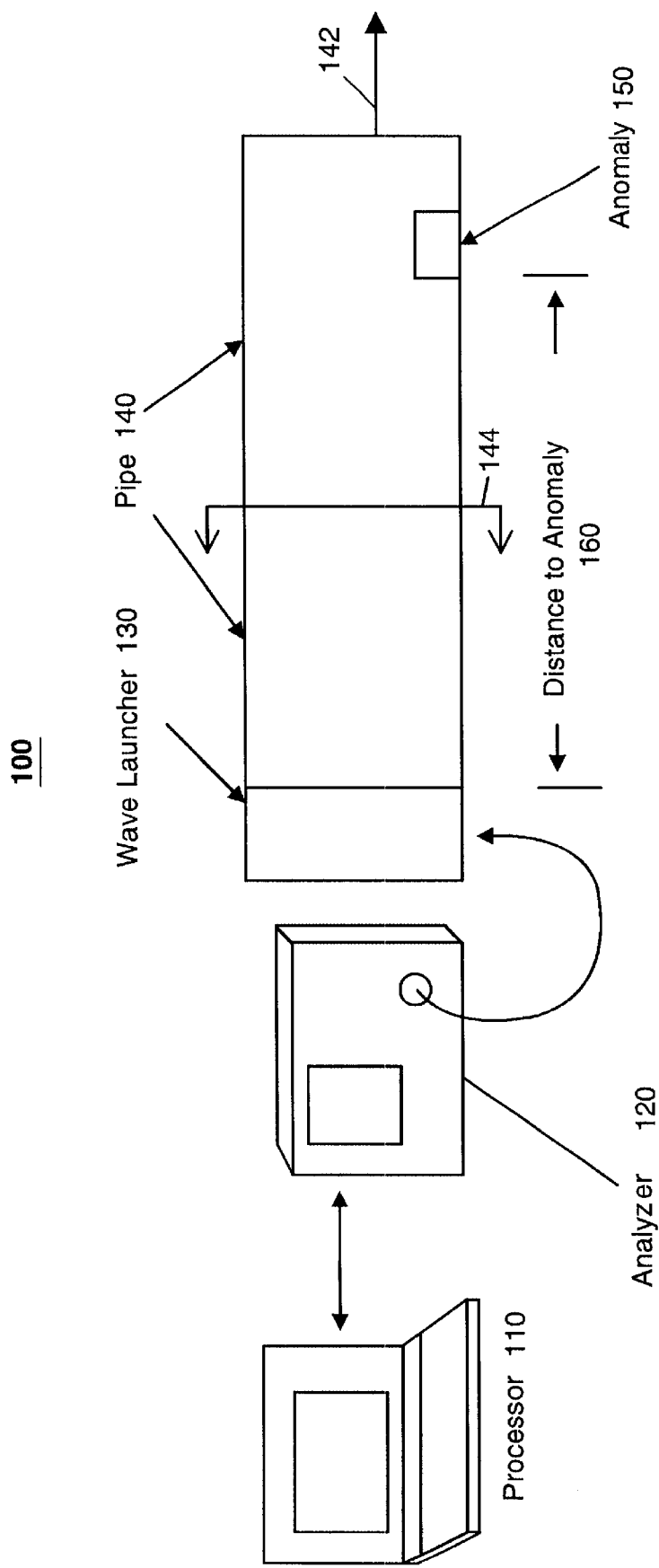
FIG. 1A is a conceptual block diagram depicting the use of a pipe inspection system constructed in accord with an illustrative embodiment of the invention.

FIG. 1A is a conceptual block diagram depicting an illustrative system 100 for inspecting characteristics of a pipe 140. As mentioned above, the term pipe refers collectively to a pipe, pipeline, pipe section and pipeline section, and, unless otherwise specified, aspects of the invention are applicable both to pre-installation/laying quality assurance testing as well as to post-installation/laying anomaly detection. The illustrative inspection system 100 includes a processor 110, an analyzer 120, and a wave launcher 130. In another embodiment, the processor 110 is incorporated within the analyzer 120, thereby eliminating the external connection between the two devices. In a further embodiment, the processor 110, the analyzer 120, and the wave launcher 130 are incorporated within a single device. As skilled artisans will appreciate, various components of the inspection system 100 can be implemented in hardware, software or both, and that particular physical divisions between components in the illustrative embodiments should not be considered in a limiting fashion.

The pipe 140 is included in FIG. 1A for clarity, but it is not a component of the illustrative inspection system 100. Preferably, the inner surface of the pipe 140 is sufficiently conductive to support input waveforms and functions as a waveguide for a suitable axial distance along the pipe 140. As skilled artisans will appreciate, a sufficiently conductive material may be any of one of a variety of materials, such as, but not limited to, iron, steel, cobalt, nickel, alloys thereof, carbon fibers and polymeric materials. A pipe can be of any length and/or shape. By way of example, a pipe may have an ovular or rectangular cross-sectional geometry, may be several hundred or thousand feet in length, as in the case of a pipe that is being or has previously been laid, or tens of feet, such as typical lengths of pipe being quality assurance tested prior to installation.

As discussed more fully below, the wave launcher 130 transmits an input waveform along a central longitudinal axis 142 of the pipe 140. In one embodiment, the wave launcher 130 is an antenna. The analyzer 120, which is in communication with the wave launcher 130, generates an input waveform and transmits it to the wave launcher 130. According to the illustrative embodiment, the input waveform is a wideband waveform, which is a waveform having a bandwidth that forms at least about 0.1% of its center frequency. An example of a wideband waveform is a waveform which distributes its energy substantially uniformly between 250 MHz and 750 MHz, having a ratio of bandwidth to center frequency equal to about 1.0 [(750−250) 500=1.0)]. In exemplary embodiments, the system 100 employs input waveforms having a center frequency of about 800 MHz and a bandwidth of about 400 MHz. Examples of potential input waveforms include, but are not limited to, electromagnetic and acoustic waveforms.

The processor 110, which is in communication with the analyzer 120, processes and outputs results of the inspection of the pipe 140. According to one illustrative embodiment and as discussed further below, the characteristic to be detected is the curvature of the pipe 140 along the longitudinal central axis 142. According to another illustrative embodiment, the characteristic to be detected is the diameter of the pipe 140. In a further illustrative embodiment, the characteristic to be detected is the shape of a cross-sectional view of the pipe 140, taken for example along view 144. According to the illustrative embodiment of FIG. 1A, the characteristic of the pipe 140 to be detected is an anomaly 150 in the pipe 140. In one embodiment, the anomaly 150 is an obstruction. In other embodiments, the anomaly 150 may be a flange, rust, partly constructed welds, or the like. In some embodiments, the anomaly is a deformity in the pipe. In operation, the inspection system 100 detects an illustrative anomaly 150 of the pipe 140 that is located a distance 160 away from the wave launcher 130. In operation, the analyzer 120 selects the amount of input energy to transmit along the pipe 140.

In an alternate embodiment, the inspection system 100 determines from one known point the location of any other point along the pipe 140. According to another embodiment, the inspection system 100 determines the shape (i.e., curvature) of the pipe 140.

Figure 1B:
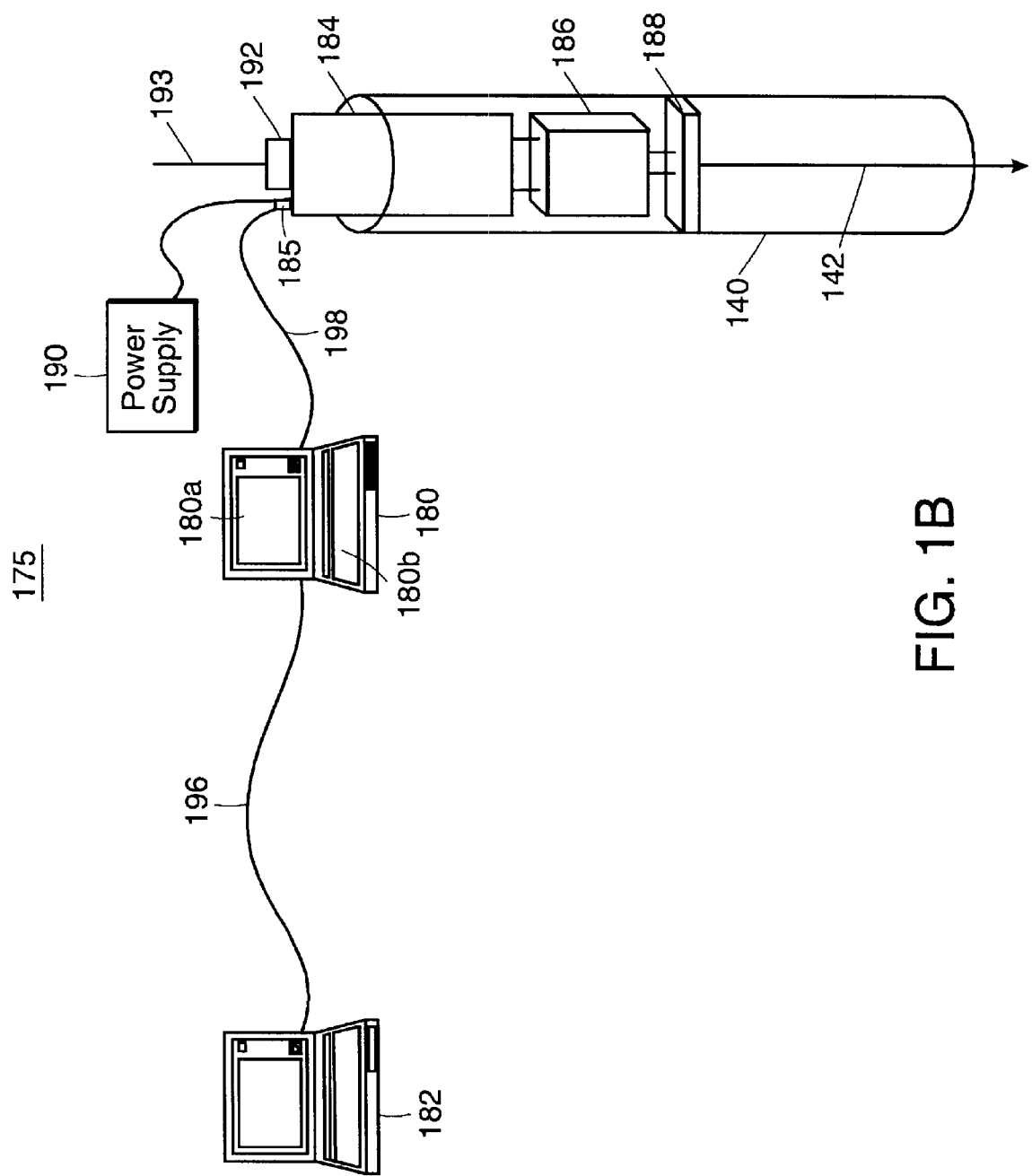
FIG. 1B is a conceptual block diagram depicting an alternative embodiment of a pipe inspection system according to an illustrative embodiment of the invention.

FIG. 1B is a conceptual block diagram depicting an alternative pipe inspection system 175 according to an illustrative embodiment of the invention. The alternative inspection system 175 includes a pipe welding processor 180, a remote processor 182, a clamp 184, an integrated analyzer 186, and an integrated wave launcher 188.

The pipe welding processor 180 includes a display 180a and a keyboard 180b. Further, the pipe welding processor 180 can be programmed to automatically initiate inspection of the pipe 140 or to enable a user to initiate a pipe inspection, for example, by way of the keyboard 180b. Like the processor 110, the pipe welding processor 180, which is in communication with the integrated analyzer 186, performs the data processing required to determine the nature of any pipe characteristics of interest. The pipe welding processor 180 displays inspection results to an operator via the display 180a and/or outputs or transmits the results via any conventional means.

The pipe welding processor 180 is analogous to the processor 110 of FIG. 1A. Like the processor 110, the pipe welding processor 180 enables an operator to initiate an inspection of the pipe 140 and performs the same function as the processor 110. Thus, any reference below to either processor 110, 180 can equally be interchanged with a reference to the other processor 180, 110. Moreover, the alternative inspection system 175 of FIG. 1B is analogous to the inspection system 100 of FIG. 1A. Thus, any reference below to either inspection system 100, 175 can equally be interchanged with a reference to the other inspection system 175, 100.

In one illustrative embodiment, the systems of FIGS. 1A and 1B operate on a barge (described below with respect to FIG. 14) adapted for laying a pipe along a bed of a body of water, such as an ocean, sea, bay, lake, river or the like. Such barges can be hundreds of feet long, with the pipe inspection systems of FIGS. 1A and 1B located at one end of the barge, and the control room for the barge located at the opposite end of the barge. Thus, the system 175 includes the remote processor 182. The remote processor 182 communicates with the pipe welding processor 180 by any conventional means (e.g., a first communications link 196), and performs substantially the same functions as the pipe welding processor 180. Consequently, any reference below to any of the processors 110, 180, 182 can equally be substituted by a reference to any of the other processors 110, 180, 182. In this way, the personnel tasked with controlling operation of the barge can also control pipe inspection and have undelayed access to pipe inspection results.

In addition to communicating with the remote processor 182, the pipe welding processor 180 also connects to the clamp 184 by any conventional means (e.g., a second communications link 198). The clamp 184, which is also referred to as an alignment tool, is a device that secures two sections of the pipe 140 together. For instance, an operator of the system 175 uses the clamp 184 to secure two sections of pipe 140 when welding the sections together. The clamp 184 can secure the sections of the pipe 140 together via mechanical means, grappling means, frictional means, electrical means, suction, magnetic means, and the like. For example, the clamp 184 can secure the sections of the pipe 140 together using clasps, magnets (if the pipe 140 exhibits magnetic properties), suction cups, and the like.

A power supply 190 provides power to the processors 180, 182, the clamp 184, the integrated analyzer 186, and the wave launcher 188. Alternatively, each of the above mentioned components has a local, independent power supply 190. For instance, the clamp 184 connects to the power supply 190 when the clamp 184 employs magnetic means or electrical means to secure sections of pipe 140 together. In one embodiment, the power supply 190 is a battery. In another embodiment, the power supply 190 is a generator.

In one embodiment, the clamp 184 also includes a clamp connection terminal 185. As illustrated, the power supply 190 and the second communications link 198 connect to the clamp connection terminal 185 to supply power to the components 184, 186, 188 and to enable communications between the processors 180, 182 and the components 184, 186, 188.

The clamp 184 also includes a connector 192. The operator connects to the connector 192 via an umbilical 193. The umbilical 193 may be made from a variety of materials, such as plastic, rubber, fiber, rope, and the like. In one embodiment, the umbilical 193 has a mating connector (shown as mating connector 194 in FIG. 1C) attached to the end of the umbilical 193 and configured to mate, or attach, with the connector 192. For example, the connector 192 may be a female connector, with the umbilical 193 having a male mating connector positioned at the end of the umbilical 193. Alternatively, the end of the umbilical 193 itself is the piece that mates with the connector 192. More specifically, the connector 192 includes an opening (not shown) for connection with the umbilical 193.

Moreover, the connector 192 may be "keyed" to accept only a certain type of umbilical 193 (e.g., an umbilical 193 having one or more particular features). For instance, the connector 192 only connects to an umbilical 193 that ends with a particular orientation (e.g., diamond end, square end, triangular end, hexagonal end). Once inserted, the umbilical 193 locks with the connector 192 to prevent loosening and/or freeing of the umbilical 193. In one embodiment, the operator uses the pipe welding processor 180 to transmit a command to the connector 192 to release its hold on the umbilical 193. In another embodiment, the connector 192 releases its hold on the umbilical 193 after a predetermined amount of time has elapsed. In yet another embodiment, the connector 192 releases its hold on the umbilical 193 when the operator removes power from the connector 192.

Once the operator removes the clamp 184, as described further below with respect to FIG. 1C, the pipe welding processor 180 communicates (e.g., over the second communications link 198) with the integrated analyzer 186.

The integrated analyzer 186 and the integrated wave launcher 188 are positioned inside the pipe 140. The walls of the pipe 140 provide protection to these integrated components 186, 188 from the external environment. This is especially advantageous when using these electronic components 186, 188 in a "hostile" environment, such as in an area subjected to heavy winds, falling stones, sand blowing, and the like. These external factors typically provide a risk of damage to the analyzer 120 and/or the wave launcher 130 located outside of the pipe 140, as shown in FIG. 1. To abate such risks, the operator of the system 175 positions the integrated components 186, 188 inside the pipe 140.

Figure 1C:
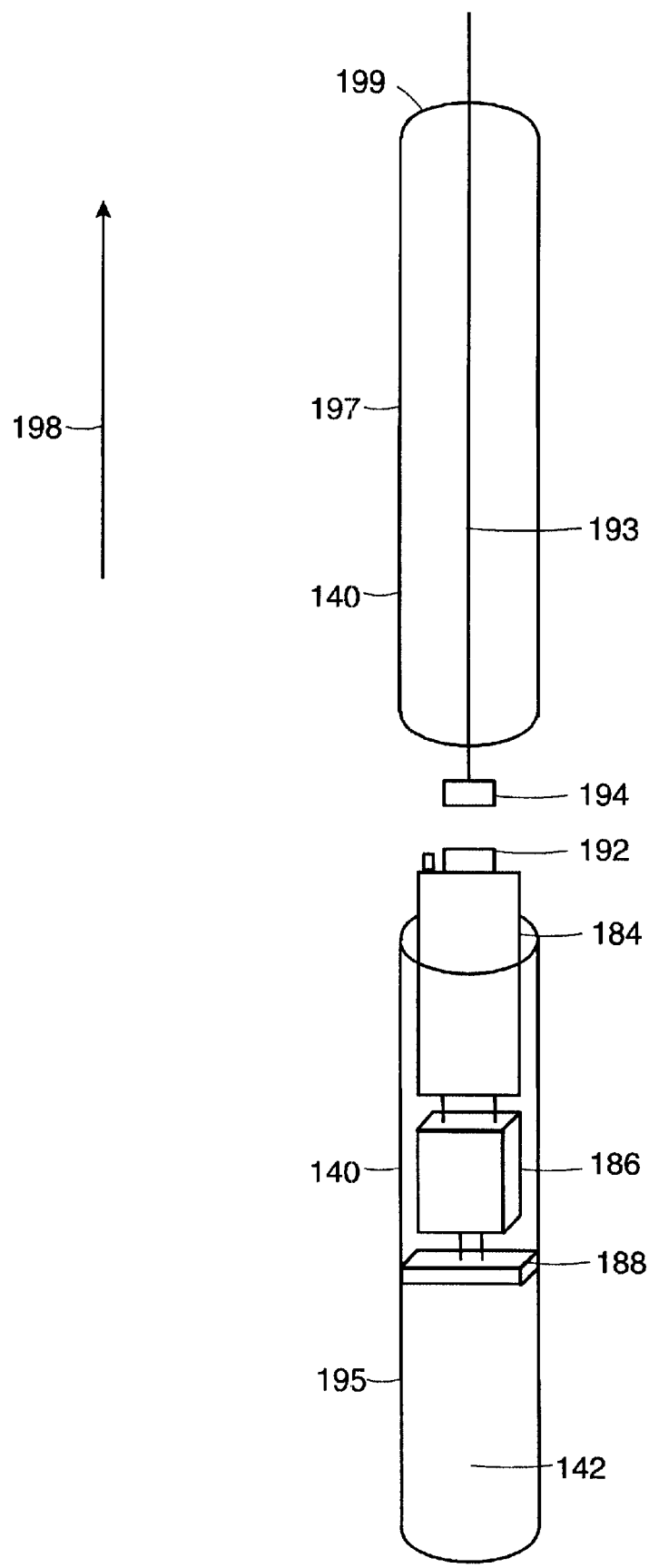
FIG. 1C is a conceptual block diagram depicting an embodiment of the operation of an exemplary clamp of the type depicted in the system of FIG. 1B.

In operation and additionally referring to FIG. 1C, in one embodiment the operator of the system 175 positions the clamp 184, the integrated analyzer 186, and the integrated wave launcher 188 in a first section 195 of the pipe 140. To clear the opening of the first section 195, the operator then removes the umbilical 193 from the connector 192 (e.g., by removing power supplied to the connector 192). The operator then introduces a second section 197 of the pipe 140 to the first section 195 for future attachment. In particular and in one embodiment, the operator lines up the two sections 195, 197 of pipe and positions the second section 197 a particular distance (e.g., two to three meters) away from the first section 195.

In one illustrative embodiment in which an operator stacks the first section 195 and the second section 197 vertically (with the second section 197 above the first section 195), an operator operates a winch that lowers the umbilical 193 from insertion at the far end 199 to the junction between the first section 195 and the second section 197. In a further embodiment, the operator determines the length (e.g., 48 meters) of the second section 197 and lowers the umbilical 193 a predetermined length beyond the length of the second section 197 so that the umbilical 193 extends beyond the second section 197, as shown in FIG. 1C.

More specifically, in one illustrative embodiment the pipe welding processor 180 transmits a command to the integrated analyzer 186 over the second communications link 198 to transmit an input waveform along the first section 195 of pipe 140 (and along any other sections of pipe welded to the first section 195 of the pipe 140 (e.g., below the first section 195). The integrated analyzer 186 collects data, as described in greater detail below, and transmits the data to the pipe welding processor 180 for storage and/or processing. An operator (i.e., usually a second operator) stationed at the junction between the two sections 195, 197 removes the second communications link 198 and the power supply connection from the clamp connection terminal 185 and then connects the umbilical 193 (i.e., the mating connector 194) with the connector 192. The umbilical 193 then provides power to the components 184, 186, 188 of the pipe inspection system 175 and enables communications between the components 184, 186, 188 and the processors 180, 182 (i.e., connects to the second communications link 198).

In one illustrative embodiment, the pipe inspection system 175 uses the data that the integrated analyzer 186 transmits to the pipe welding processor 180 to determine characteristics of external factors exerted on the pipe 140 and/or each section 195, 197 of the pipe 140. For example, the pipe inspection system 175 determines the stress associated with the pipe 140 and/or the stresses associated with the sections 195, 197 of pipe 140 as the operators construct the pipe 140 from sections of pipe 140. In further embodiments, the pipe welding processor 180 transmits a command to the integrated analyzer 186 to continuously transmit waveforms along the pipe 140 (and sections 195, 197 of pipe) to collect data during the entire construction and/or deployment process of the pipe 140.

Once the connection is made, the operator lowers the second section 197 to make contact with the first section 195. The clamp 184 then secures the second section 197 of the pipe 140 with the first section 195 of the pipe 140 via the mechanism described above (e.g., magnetics) and a welder welds the sections 195, 197 together.

Once the welding is complete, the operator of the inspection system 175 causes the clamp 184 to release its hold on the two sections 195, 197. For example, the operator removes power from the clamp 184 by shutting off the power supply 190 (not shown) to enable the clamp 184 to release its hold on the two sections 195, 197.

In another embodiment, the pipe welding processor 180 transmits a signal to the clamp 184 when the welding process is complete. The signal causes the clamp 186 to release its hold on the two sections 195, 197 of the pipe 140. In one embodiment, the pipe welding processor 180 transmits the signal after a certain time period has elapsed. Alternatively, the pipe welding processor 180 transmits the signal upon an input command by the operator via the keyboard 180*b*. In yet other embodiments, the operator of the system 175 is positioned in the control room of the barge and consequently uses the remote processor 182 to transmit the signal to the clamp 184 release its hold on the sections 195, 197.

To use the inspection system 175 to inspect both sections 195, 197 of the pipe 140, the operator then pulls the umbilical 193 so that the connector 192, the clamp 184, the integrated analyzer 186, and the wave launcher 188 all slide along the pipe 140 until the clamp 184 reaches the far end 199 of the second section 197 of the pipe. The direction of movement of these components 184, 186, 188, 192 is shown with arrow 198.

The clamp 184 is now in a position to secure a third section of pipe 140 that connects to the second section 197. If an operator introduces a third section (not shown), a welder welds the third section to the second section 197 of the pipe 140 and the operator then moves the components 184, 186, 188, 192 to the far end of the third section. Thus, the integrated analyzer 186 and the integrated wave launcher 188 are in a position to inspect the entire pipe 140 for anomalies 150 following the attachment of additional sections of pipe 140.

As described in more detail below with respect to FIGS. 6A and 6B, and similar to the analyzer 120 described above in FIG. 1A, the integrated analyzer 186 provides an input waveform to the integrated wave launcher 188. Because the integrated analyzer 186 provides the same function as the analyzer 120, any and all references to either analyzer 120, 186 above and below can be replaced by a reference to the other analyzer 186, 120 without departing from the spirit and scope of the invention.

Similar to the wave launcher 130, the integrated wave launcher 188 connects to the pipe 140 and is adapted to transmit an input waveform having a selected input energy along the central longitudinal axis of the pipe 140. Because the integrated wave launcher 188 provides the same function as the wave launcher 130, any and all references to either wave launcher 130, 188 above and below can be replaced by a reference to the other wave launcher 188, 130 without departing from the spirit and scope of the invention.

Figure 2:
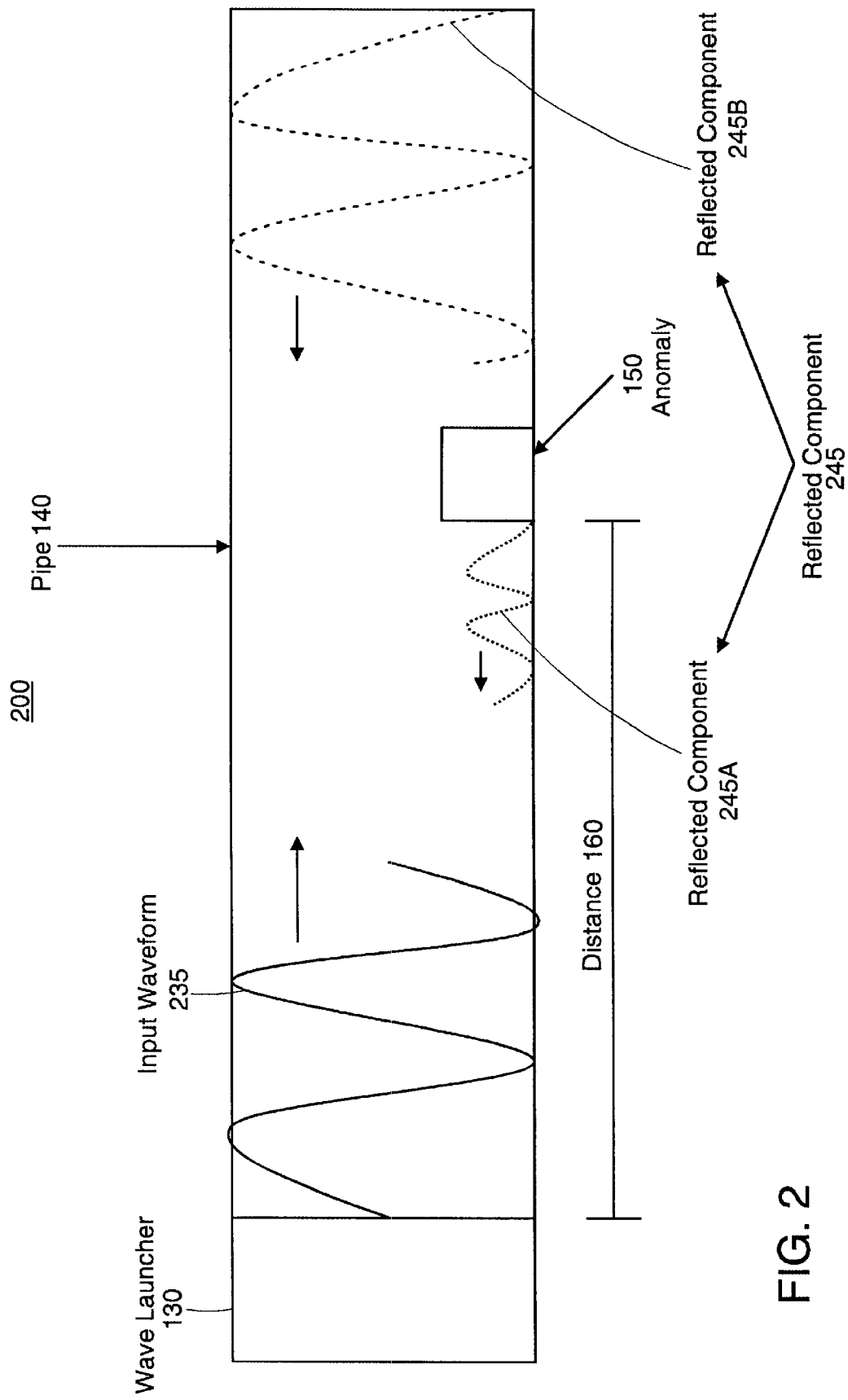
FIG. 2 is a conceptual diagram depicting illustrative waveforms transmitted from and received by an exemplary wave launcher of the type depicted in the systems of FIGS. 1A and 1B.

FIG. 2 is a conceptual diagram 200 depicting an illustrative input waveform 235 transmitted from the wave launcher 130, along with an exemplary reflected component 245. As depicted in FIG. 2, the analyzer 120 generates the input waveform 235 corresponding to a selected input energy. The analyzer 120 transmits the input waveform 235 to the wave launcher 130, and the wave launcher 130 then launches the input waveform 235 along the longitudinal central axis 142 (not shown) of the pipe 140. After sending the input waveform 235 into the pipe 140, the wave launcher 130 receives a reflected component 245 of the input waveform 235. The reflected component 245 includes a reflected component 245A and a reflected component 245B. The reflected component 245A is the component of the input waveform 235 that the anomaly 150 reflects towards the wave launcher 130. The reflected component 245B is the component of the input waveform 235 that the end wall 241 of the pipe 140 reflects towards the wave launcher 130. The reflected component 245 of the input waveform 235 has a characteristic reflected energy that depends on the characteristics of the anomaly 150, the characteristics of the pipe 140, the distance 160 between the wave launcher 130 and the anomaly 150, and other attributes of the illustrative inspection system 100 and pipe 140. These dependencies are further described below.

Once the wave launcher 130 receives the reflected component 245 of the input waveform 235, the wave launcher 130 transfers it to the analyzer 120. The analyzer 120 determines the characteristic reflected energy of the reflected component 245 and transmits the reflected energy and the input energy to the processor 110. The processor 110 compares the input energy and reflected energy to determine the attributes of the anomaly 150. The attributes of the anomaly 150 may be any one of a variety of attributes, such as, but not limited to, the size of the anomaly 150, the type of anomaly 150 (e.g., defect, flange, rust, etc.), and the distance 160 to the anomaly 150. The processor 110 then reports its results on an output device connected to the processor 110 such as a printer, display or any other connection means. In the case of the system 175, the pipe welding processor 180 also provides the inspection results to the remote processor 182 via a convention communication means (e.g., the first communications link 196).

According to a further feature, the illustrative processor 110 begins by calibrating the analyzer 120 for measurement. In one embodiment, the processor 110 calibrates the analyzer 120 by temperature stabilizing the analyzer 120. Temperature stabilizing includes an operator of the illustrative system 100, 175 positioning the analyzer 120 in a temperature cycling chamber. In one embodiment, the temperature cycling chamber is an enclosed, insulated area that introduces devices such as an analyzer 120 to a range of temperatures. The processor 110 is positioned outside of the temperature cycling chamber. The processor 110 loads from its processor memory (e.g., ROM, RAM) a test program at which the analyzer 120 can perform several functions and operations specified in the test program. For example, the processor 110 may request the analyzer 120 to perform the operations corresponding to the future operations that the analyzer 120 will carry out. Alternatively, the processor 110 may request the analyzer 120 to perform a diagnostic test on the components of the analyzer 120.

The processor 110 begins this test program and subsequently introduces the analyzer 120 to a range of temperatures while the analyzer 120 is in operation. Once the analyzer 120 is subjected to the entire range of temperatures, it becomes temperature stabilized and it transmits the results from the test program to the processor 110. The processor 110 receives and stores the results of the analyzer 120 running this test program. When the illustrative inspection system 100 is later positioned at the pipe 140, the processor 110 measures the ambient temperature at the pipe 140. The processor 110 then retrieves the stored results for the analyzer 120 from the temperature cycling test program for the ambient temperature. The processor 110 then initializes the analyzer 120 by using the stored results for the ambient temperature.

In another embodiment, the processor 110 calibrates the analyzer 120 every time the analyzer 120 is powered up. As described above, the processor 110 measures the ambient temperature of the pipe 140 and executes the test program on the analyzer 120. The analyzer 120 executes the test program at the current temperature and then transfers the results to the processor 110. The processor 110 compares these results with expected results at the ambient temperature to obtain a temperature error associated with the analyzer 120. In one embodiment the processor 110 calibrates the analyzer 120 in this fashion every time the temperature at the location at which the illustrative inspection system 100 is used varies from the previous temperature at the previous location. In a further embodiment, the processor 110 calibrates the analyzer 120 in this fashion whenever the analyzer 120 is powered down and then powered up. In a further embodiment, the processor 110 alerts the operator of the illustrative system 100 when the temperature error is above a predetermined temperature error threshold.

According to another embodiment, the processor 110 calibrates the analyzer 120 by temperature stabilizing the analyzer 120 in a thermostatically-controlled chamber. In one embodiment, the thermostatically-controlled chamber is a temperature cycling chamber, as described above, operating at a continuous, constant temperature. By way of example, the thermostatically-controlled chamber operates at 25° Celsius. The operator of the illustrative system 100 positions the analyzer 120 in the thermostatically-controlled chamber and the inspection system 100 begins normal execution. In a further embodiment, the processor 110 compares the output of the analyzer 120 at the constant temperature with expected results at the same constant temperature to obtain a temperature error associated with the analyzer 120. In a further embodiment, the processor 110 displays a warning to the operator of the illustrative system 100 when the temperature error is above a predetermined temperature error threshold. Alternatively, the processor 110 initializes the analyzer 120 with one of the calibration techniques described above or below when the temperature error is above the predetermined threshold.

In the illustrative embodiment, once calibration is complete, the processor 110 instructs the analyzer 120 to generate the input waveform 235 which is transmitted along the pipe 140. The analyzer 120 may generate the input waveform 235 using a signal generator. Alternatively, the analyzer 120 may use an acoustic transducer to apply a force to the pipe 140 to generate a sound wave as the input waveform 235. The processor 110 indirectly selects the input energy of the input waveform 235 by selecting the frequency of the input waveform 235. Before transmitting the input waveform 235 to the wave launcher 130, the analyzer 120 determines the input energy associated with the input waveform 235.

As discussed in more detail below with respect to FIG. 6A, after the analyzer 120 determines the input energy for the input waveform 235, the analyzer 120 transmits the input waveform 235 to the wave launcher 130. The wave launcher 130 in turn launches the input waveform 235 along the central axis 142 of the pipe 140. Then, the wave launcher 130 receives the reflected component 245 of the input waveform 235 and sends it to the analyzer 120.

Once the analyzer 120 receives the reflected component 245, it determines a transfer function relating the input energy corresponding to the input waveform 235 with the reflected energy corresponding to the reflected component 245 of the input waveform 235. The analyzer 120 determines a transfer function for each reflected component 245 (e.g., reflected component 245A and 245B) of the input waveform 235. The transfer function of energy is denoted by the following equation:

$$\text{transfer function} = \frac{E_{reflected}}{E_{input}}.$$

Once the analyzer 120 determines a transfer function for the input energy and the reflected energy corresponding to the reflected components 245A and 245B, it transmits these transfer functions to the processor 110. The processor 110 then performs the necessary data processing to determine parameters of the characteristic of interest.

Figure 3:
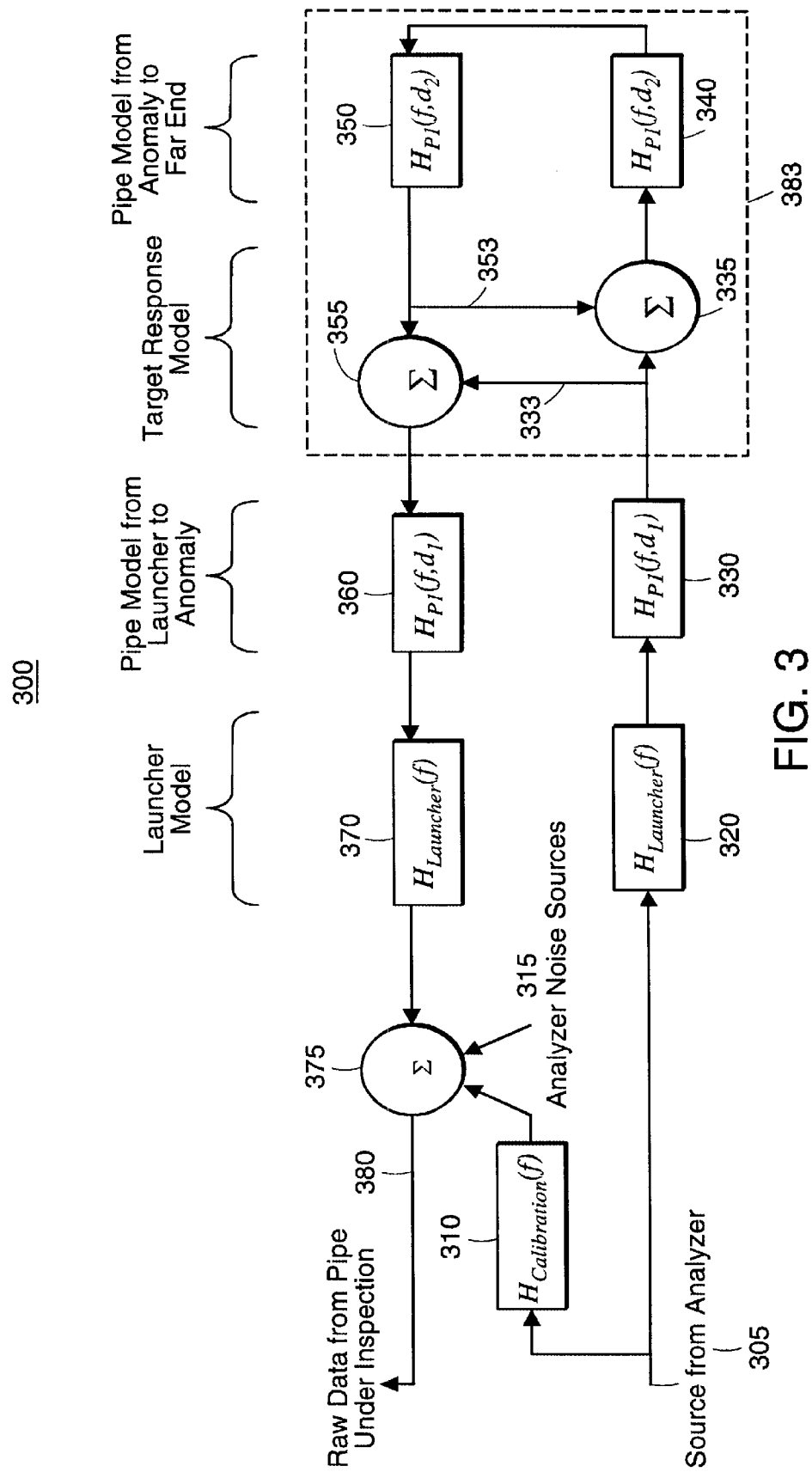
FIG. 3 depicts an equivalent model of the systems of FIGS. 1A and 1B according to an illustrative embodiment of the invention.

FIG. 3 is a diagram depicting an equivalent model 300 of the illustrative inspection systems 100 and the pipe 140 of FIGS. 1A and 1B. The processor 110 determines the energy reflected from the anomaly 150 by generating a mathematically modeled pipe that is representative of the pipe 140. The analyzer 120 simulates the input waveform 235 that is transmitted along the pipe 140 as a model input waveform 305. The model input waveform 305 is shown at the lower left corner of FIG. 3. The analyzer 120 transmits the model input waveform 305 to the wave launcher 130 in preparation for the launching of the model input waveform 305 along a longitudinal axis of the model pipe. According to one embodiment, the model pipe has a substantially round cross-sectional shape and the longitudinal axis is the central longitudinal axis. As a result of imperfections in test port cables and other calibration effects, a calibration component 310 of the model input waveform 305 is substantially immediately reflected back to the analyzer 120. This calibration component 310 and the energy associated with the calibration component 310 is represented in FIG. 3 as $H_{Calibration}(f)$.

A first remainder 320 and a second remainder 330 of the model input waveform 305 are transmitted through the wave launcher 130 and travel the distance 160 to the model anomaly 335, or model target. The remainders 320 and 330 are represented in FIG. 3 as $H_{Launcher}(f)$ and $H_{P1}(f, d_l)$, respectively. The wave launcher 130 has intrinsic losses associated with it, and so when the model input waveform 305 is transmitted through the wave launcher 130 into the model pipe, a reflected wave launcher portion 370 of the model input waveform 305 is reflected toward the analyzer 120.

At the distance 160, the model anomaly 335 causes a first model reflected component 333 of the model input waveform 305 to be reflected toward the wave launcher 130. The first model reflected component 333 represents the reflected component 245A shown in FIG. 2. A third remainder 340 of the model input waveform 305 continues along the model pipe until it reaches the end of the model pipe. A second model reflected component 350 is then reflected toward the wave launcher 130 when it reaches the end wall of the model pipe, and this second model reflected component 350 represents the reflected component 245B. The second model reflected component 350 and the energy corresponding to this reflected component 350 is represented in FIG. 3 by $H_{P2}(f, d_2)$. The sum of the model reflected components 333, 350 are combined at a first summation block 355 and the resulting sum 360 is transmitted to the analyzer 120. The resulting sum 360, which is shown in FIG. 3 as $H_{P1}(f, d_l)$, is transmitted through the wave launcher 130. Additionally, the model anomaly 335 reflects a portion of the second model reflected component 350 (that was reflected by the end wall of the model pipe) back toward the end wall, creating a third model reflected component 353.

The wave launcher 130 transmits the resulting sum 360 and the reflected wave launcher portion 370 toward the analyzer 120. The resulting sum 360 and the reflected wave launcher portion 370 are combined with the calibration component 310 and any analyzer 120 noise sources 315 at a second summation block 375. A total model reflected component 380 is then transmitted to the analyzer 120. Therefore, the total model reflected component 380 includes a reflected component corresponding to the wave launcher 130 (e.g., reflected wave launcher portion 370), the model anomaly 335 (e.g., first model reflected component 333), the end wall of the model pipe (e.g., second model reflected component 350), the calibration effects (e.g., calibration component 310), and any noise associated with the analyzer 120 (e.g., analyzer 120 noise sources 315).

As described in more detail below with respect to FIG. 6A, the analyzer 120 receives the total model reflected component 380 and calculates a model transfer function relating the model input energy with the model reflected energy corresponding to the total model reflected component 380. The analyzer 120 then transfers this model transfer function to the processor 110. The processor 110 compares the transfer function associated with the reflected energy of the reflected component 245 to the model transfer function corresponding to the total model reflected component 380. From this comparison, the processor 110 determines the location 160 and size of the anomaly 150 and reports these results on an output device.

In one embodiment, the processor 110 includes the calibration component 310 of the analyzer 120, the response of the wave launcher 130, and the response of the pipe 140 stored in its local memory (e.g., RAM, ROM). The analyzer 120 noise may be negligible if the pipe 140 reflects most of the input waveform 235. In this situation, the processor 110 can detect an anomaly 150 at virtually unlimited range. In another embodiment, the processor 110 accounts for the analyzer 120 noise when the analyzer 120 receives the reflected component 245.

In another embodiment, the processor 110 repeats a portion of the equivalent model 300 to obtain a more accurate total model reflected component 380. For instance, the processor 110 can repeat the block 383. The processor 110 typically repeats the block 383 to model the pipe 140 when the pipe 140 has multiple anomalies 150. In one embodiment, an operator inputs the estimated number of anomalies 150 to model. In another embodiment, the processor 110 models the pipe 140 using a predetermined number of repeated blocks 383 as a default setting to accurately model multiple anomalies 150. If the number of repeated blocks 383 is greater than the number of actual anomalies 150, the model reflected components 333 and 350 for a non-existent anomaly 150 are substantially zero, and therefore, do not contribute to the resulting sum 360.

Illustratively, to process the calculations and modeling as described above, the processor 110 has digital signal processing capabilities that are used in a collection of DSP algorithms (discussed in further detail below). In one embodiment, the processor 110 uses an ideal lossless physics-based model as the hypothetical model to represent a pipe 140 with no contaminants, defects, anomalies, or other losses. The model pipe has uniform quality of construction material, an identical cross-section along the entire length of the model pipe, and a perfectly conductive inner surface. The processor 110 determines the response of the model pipe and subsequently determines the type of the anomaly 150 and the location 160 of the anomaly 150 within the pipe 140 by comparing the actual reflected energy of the pipe 140 with the modeled reflected energy of the ideal pipe 140. In another embodiment, the processor 110 uses an ideal lossy physics-based model. In this embodiment, the processor 110, assumes a pipe 140 having a conductive inner surface that experiences greater losses relative to the conductivity of the inner surface of the model pipe.

Figure 4:
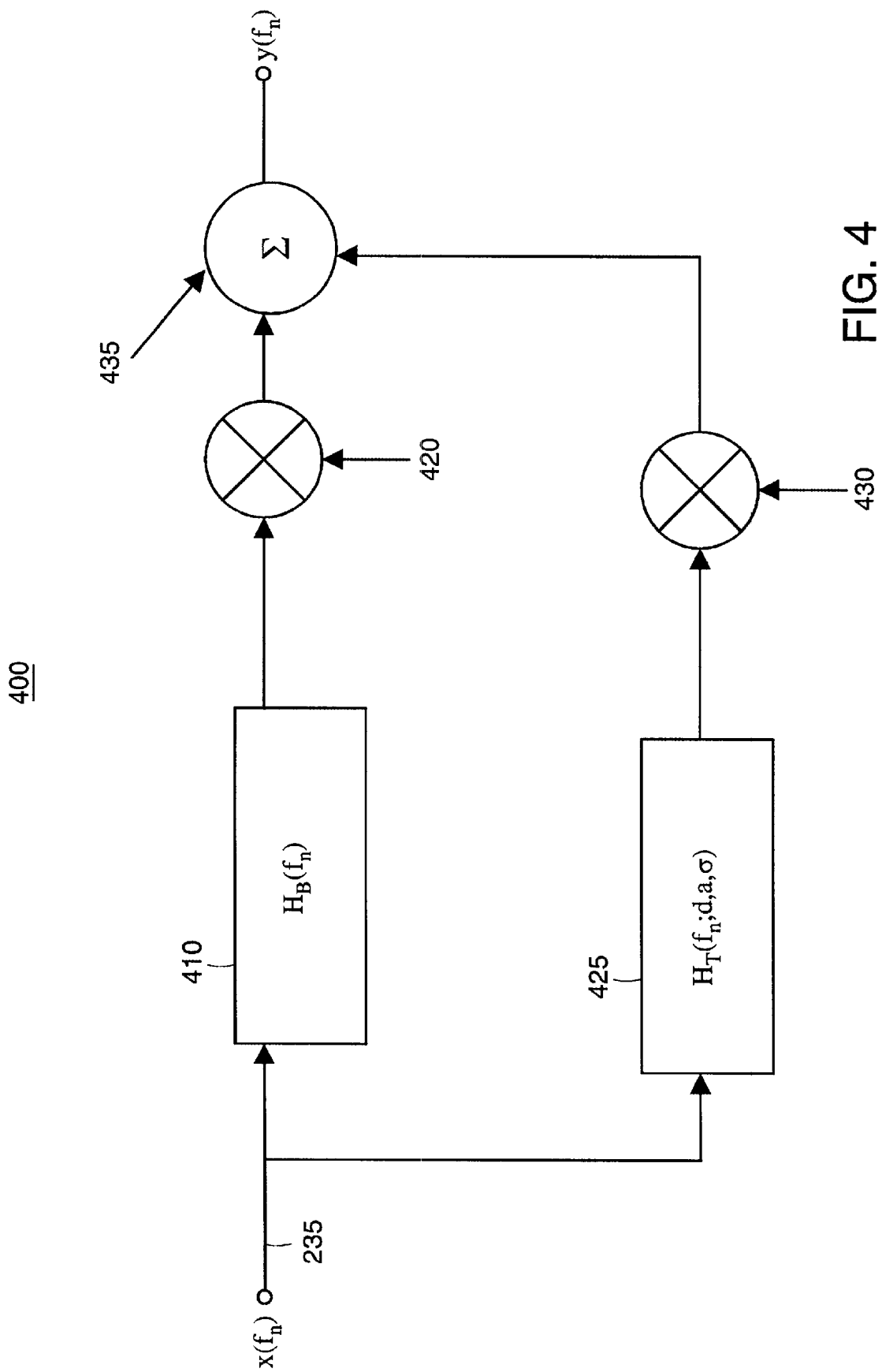
FIG. 4 is a block diagram showing an illustrative lossy physics-based model of the systems of FIGS. 1A and 1B.

FIG. 4 is an illustrative block diagram showing a lossy physics-based model 400 of the inspection systems 100 and 175 incorporating partial a priori knowledge. As previously described, the analyzer 120 generates a series N of input waveforms 235 and applies these input waveforms 235 to the wave launcher 130. The amplitude $x(f_n)$, $n=0,1,\ldots,N-1$, of the input waveforms 235 is a function of its excitation frequency. The model 400 also includes the reflection response 410 of the wave launcher 130 and other near-field effects (i.e., the effects on the electric and magnetic fields of the reflected component 245 when the reflected component 245 is within the range of the wave launcher 130), denoted below by $H_B(f_n)$. When reflected toward the wave launcher 130, the input waveform 235 further experiences a scaling coefficient 420 for near-field effects, represented below by $K_B$. The scaling coefficient 420 adjusts the magnitude and phase of the reflected component 245.

The processor 110 models the pipe 140 as a lossy physics-based model 425, shown as $H_T(f_n; d, \alpha, \sigma)$. The lossy physics-based model 425 of the pipe 140 depends on several parameters of the pipe 140, such as, but not limited to, the round-trip distance d between the anomaly 150 and the wave launcher 130, the radius $\alpha$ of the pipe 140, the effective conductance $\sigma$ of the inner surface of the pipe 140, the scaling coefficient 430 $K_T$ for the anomaly 150, and the background noise 435 $\eta(f_n)$ of the analyzer 120.

The wave launcher 130 receives the reflected component 245 of each input waveform 235. The amplitude $y(f_n)$ of the reflected component 245 is also a function of the excitation frequency of the input waveform 235. The analyzer 120 calculates an estimate of the transfer function of the system 100 or 175. As described above, the transfer function is given as:

$$H(f_n) = \frac{y(f_n)}{x(f_n)}. \tag{1}$$

The processor 110 then operates on the transfer function $H(f_n)$ to locate and identify any anomalies 150 within the pipe 140. Under the assumption that the background noise $\eta(f_n)$ is a zero-mean, independent, complex, Gaussian process, the processor 110 employs a minimum mean-squared error estimate, given as:

$$J_{min} = \sum_{n=0}^{N-1} \left| H(f_n) - \hat{K}_B H_B(f_n) - \hat{K}_T H_T(f_n; \hat{d}, \hat{a}, \hat{\sigma}) \right|^2. \tag{2}$$

Note, following standard convention, the carat (^) calls attention to an estimated value of a parameter (as opposed to its "true" value).

To begin signal processing, the processor 110 assumes a range of distances over which to search for anomalies 150 within the pipe 140. This range is denoted as $d_l$, $l=0,1,\ldots,L-1$, where L is the total number of steps within the range $d_l$ of distances at which to search for anomalies 150. In one embodiment, the range $d_l$ covers a few kilometers in steps of 0.1 meters. In other embodiment, the range $d_l$ covers a few meters or less. For each value of $d_l$, the pipe 140 transmission is calculated as:

$$H_T(f_n; d_l, \alpha, \sigma) = e^{-\alpha_{11} d_l} e^{-j\beta_{11} d_l}, \tag{3}$$

where $$\alpha_{11} = \sqrt{\frac{2\pi f_n}{2\sigma}} \frac{(v'_{11})^4 + a^2(2\pi f_n)^2 \varepsilon_0 \mu_0 \left(1 - \left(\frac{v'_{11}}{2\pi f_n a \sqrt{\varepsilon_0 \mu_0}}\right)^2\right)}{a^3((v'_{11})^2 - 1)(2\pi f_n)^2 \varepsilon_0 \mu_0 \sqrt{1 - \left(\frac{v'_{11}}{2\pi f_n a \sqrt{\varepsilon_0 \mu_0}}\right)^2}}, \tag{4}$$

and $$\beta_{11} = 2\pi f_n \sqrt{\varepsilon_0 \mu_0} \sqrt{1 - \left(\frac{v'_{11}}{2\pi f_n a \sqrt{\varepsilon_0 \mu_0}}\right)^2}. \tag{5}$$

In Equations (4) and (5), the new symbols are identified as:

$\epsilon_0$ Permeability of free space, $$8.854 \times 10^{-12} \frac{C^2}{N \cdot m^2},$$

$\mu_0$ Permeability of free space, $$4\pi \times 10^{-7} \frac{Wb}{A \cdot m},$$

$v_{11}$ First root of the first derivative of the Bessel function of first kind.

Given the three vectors, $H(f_n)$, $H_B(f_n)$, $H_T(f_n; d_l, \hat{a}, \hat{\sigma})$, the processor 110 calculates the inter- and intra-signal correlation functions as:

$$R_{HH} = \sum_{n=0}^{N-1} H*(f_n)H(f_n), \quad (6)$$

$$R_{H_B H_B} = \sum_{n=0}^{N-1} H_B^*(f_n)H_B(f_n), \quad (7)$$

$$R_{H_T H_T} = \sum_{n=0}^{N-1} H_T^*(f_n; d_l, a, \sigma)H_T(f_n; d_l, a, \sigma), \quad (8)$$

$$R_{H_B H_T} = \sum_{n=0}^{N-1} H_B^*(f_n)H_T(f_n; d_l, a, \sigma), \quad (9)$$

$$R_{H_T H_B} = \sum_{n=0}^{N-1} H_T^*(f_n; d_l, a, \sigma)H_B(f_n), \quad (10)$$

and the measurement correlation functions as:

$$P_{H_B} = \sum_{n=0}^{N-1} H_B^*(f_n)H(f_n), \quad (11)$$

$$P_{H_T} = \sum_{n=0}^{N-1} H_T^*(f_n; d_l, a, \sigma)H(f_n). \quad (12)$$

The signal correlation functions are used to form the correlation matrix $$R(d_1) \equiv \begin{bmatrix} R_{H_B H_B} & R_{H_B H_T} \\ R_{H_T H_B} & R_{H_T H_T} \end{bmatrix}, \quad (13)$$

while the measurement correlation functions are incorporated into the vector $$p(d_1) \equiv \begin{bmatrix} P_{H_B} \\ P_{H_T} \end{bmatrix}. \quad (14)$$

For a particular selection of distance $d_l$, the minimum mean-squared error is given as:

$$J_{min}(d_l) = R_{HH} - p^H R^{-1} p. \quad (15)$$

The associated values of the optimum scaling constants are given as $$\begin{bmatrix} K_B(d_l) \\ K_T(d_l) \end{bmatrix} = R^{-1} p. \quad (16)$$

Equations (15) and (16) are computed for all $d_l$, $l=0,1, \ldots L-1$. Once completed, the global minimum attained by $J_{min}$ is identified together with the distance $d_l$ at which it occurs, and the attendant value of $K_T$.

The magnitude of the estimate of $K_T$ is related to the cross-sectional area of the anomaly 150 as:

$$|K_T| \approx 8.3 \times T^2 + 0.5 \times T, \quad (17)$$

where T is the fractional cross-sectional area of the anomaly 150. This expression is inverted to find the size of the target 150.

To find the type of the anomaly 150, the magnitude of $J_{min}$ at its global minimum helps define the depth (i.e., distance 160 along the length of the pipe 140) of the anomaly 150. For example, since the processor 110 bases the lossy physics-based model 425 on the presumption of an anomaly 150 having "zero thickness," an anomaly 150 of substantial length provides a relatively high value at the local minimum. In one embodiment, the processor 110 displays the magnitude of $J_{min}$ at its global minimum to the operator of the system 100, 175 so that the operator can determine the type of the anomaly 150. In another embodiment, the processor 110 has a table stored in local memory associating a range of depths with a type of anomaly 150 and determines the type of anomaly 150 from the depth and the stored table.

Since $J_{min}$ is calculated as a function of distance (see Equation 15), the processor 110 determines the location 160 of the anomaly 150 from the distance $d_l$. The distance $d_l$ at which the global minimum of $J_{min}$ occurs is the maximum likelihood estimate of the target 150 location 160 from the wave launcher 130.

In an alternate embodiment, the processor 110 employs the method of maximum likelihood, which requires full knowledge of the output probability density functions, to locate and identify any and all anomalies 150 within the pipe 140.

As skilled artisans will appreciate, the processor 110 may be any one of a variety of devices, such as, but not limited to, a laptop computer with digital signal capabilities, a desktop computer, a workstation, and the like. Generally, the processor 110 can be any device that has computer memory (e.g., RAM, ROM) and digital signal processing capabilities so that the DSP algorithms can be stored and/or executed on the processor 110.

In another embodiment, the processor 110 uses an average model for the pipe 140. The processor 110 averages losses associated with construction, internal characteristics, differences within the cross section, and other losses apparent throughout the pipe 140 to obtain an average model pipe. In another embodiment, the processor 110 utilizes a section by section model of the pipe 140, in which the processor 110 segments the pipe 140 into sections and computes a representation for each of the segmented sections. The processor 110 builds a model of a portion of the pipe 140 being tested by analyzing and then joining each section of the relevant portion of the pipe 140.

According to one embodiment, the operator of the inspection system 100 selects the appropriate model (e.g., ideal physics-based system model 400, average model, section-by-section model) that the processor 110 uses to model the pipe 140 from a menu displayed on the output device, as discussed more fully below. According to another embodiment, the processor 110 determines which model to apply depending on the characteristics of the pipe 140. As described in more detail below with respect to FIG. 6A, after the processor 110 receives the transfer function relating the input energy corresponding to the input waveform 235 with the reflected energy corresponding to the reflected component 245, the processor 110 uses this data to determine which model to use in determining the characteristics of the anomaly 150.

Figure 5:
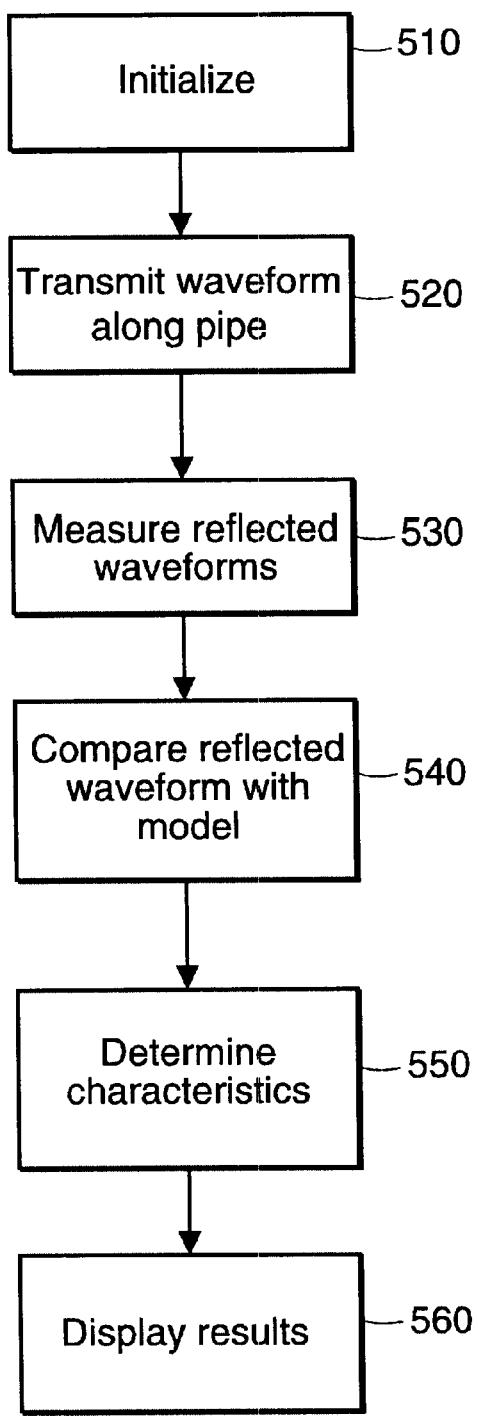
FIG. 5 is a flow diagram depicting an illustrative operation of the systems of FIGS. 1A and 1B.

FIG. 5 is a flow diagram 500 depicting an illustrative operation of the inspection system 100 of FIGS. 1A and 1B, respectively. First, the processor 110 initializes (Step 510) the analyzer 120. In one embodiment and as described above, the processor 110 temperature calibrates the analyzer 120. The processor 110 may also perform a diagnostic check on the components of the analyzer 120. Initialization may also include a combination of the techniques described above.

At step 520, the wave launcher 130 transmits the input waveform 235 along the central longitudinal axis 142 of the pipe 140. As described above, the analyzer 120 generates the input waveform 235 and transmits it to the wave launcher 130. In one embodiment, the generated input waveform 235 is an electromagnetic waveform having a selected frequency and energy. The range of frequencies at which the input waveform 235 is generated is discussed more fully below with respect to FIG. 10A. As skilled artisans will appreciate and as described more fully below, the input waveform 235 may be any one of a variety of wideband waveforms, such as, but not limited to, a chirp waveform, a spread spectrum waveform, a wavelet waveform, and a solitons waveform. In another embodiment, the input waveform 235 is an acoustic waveform.

After the wave launcher 130 transmits the input waveform 235 along the central longitudinal axis 142 of the pipe 140, the wave launcher 130 receives the reflected component 245 of the input waveform 235 and transmits it to the analyzer 120. As described above with respect to FIG. 2, the analyzer 120 measures (Step 530) the characteristic reflected energy of the reflected component 245. The analyzer 120 then determines the transfer function relating the input energy corresponding to the input waveform 235 with the reflected energy corresponding to the reflected component 245 (e.g., reflected components 245A and 245B) of the input waveform 235. The analyzer 120 then transmits the transfer function to the processor 110.

As discussed with respect to FIG. 3, the processor 110 compares (Step 540) the transfer function associated with the reflected energy of the reflected component 245 with the model transfer function corresponding to the total model reflected component 380. From this comparison, the processor 110 determines (Step 550) the location 160 and size of the anomaly 150. Although the flow diagram 500 illustrates the operation of the inspection system 100, 175 for one anomaly 150, the invention extends to a pipe 140 containing a plurality of anomalies 150. In other embodiments, step 550 may also include using the above discussed mathematical process for determining the axial shape of the pipe 140 (i.e. the curvature of the pipe 140 along the central longitudinal axis 142). Skilled artisans will appreciate that the pipe 140 need not have a circular cross-section 144 and that the location of the central axis 142 along which the input waveform 235 propagates may be adjusted to accommodate pipes 140 having non-circular cross-sections 144. As previously mentioned, in some embodiments, a user provides the measurement system 100 of the invention with cross-sectional information of the pipe 140. In other embodiments, the system 100 automatically determines the cross-section 144 of the pipe 140.

At step 560, the processor 110 displays the results on an output device to the operator of the inspection system 100. The pipe welding processor 180 also provides the results to the remote processor 182. The reported results may be any of one of a variety of statistics, such as, but not limited to, the type of the anomaly 150, the size of the anomaly 150, and the location 160 of the anomaly 150, a graphic depicting a pipe geometry substantially in real-time as a pipe is being laid, warning signals representative of a pipe deformation approaching a critical tolerance, indicators that a pipe fails to meet requisite manufacturing tolerances and the like. Examples of output devices are any one of a variety of devices such as, but not limited to, a computer monitor, a LCD screen, one or several light sources having a predefined meaning associated with the anomaly 150 (e.g., a blue light denoting that the anomaly 150 is a flange, a red light indicating that the anomaly 150 is rust, etc.), a cellular phone screen, a personal digital assistant screen, and an output device that generates predefined tones (e.g., a 40 Hz tone meaning the anomaly 150 is a flange, a 60 Hz tone meaning the anomaly 150 is rust, etc.).

In one embodiment, the processor 110 calculates structural forces being exerted on the pipe as a result of the anomaly 150. In a further embodiment, the processor 110 displays the results corresponding to the anomaly 150 in a graphical user interface (GUI). The output device associated with the processor 110 displays the GUI, and the GUI displays the anomaly 150 using, for example, color images, graphs, plots, scales, sounds, and the like to represent the location and size of the anomaly 150, and also any structural forces being applied to the pipe as a result of the anomaly 150. Alternatively, the processor 110 displays the results with an echo plot, which is a plot that displays points to trace the location 160 and size of the anomaly 150 in the pipe 140. In yet another embodiment, the processor 110 displays the results with a textual description. For example, the processor 110 reports that the anomaly 150 is a "3 cm buckle found at 10 km". The processor 110 may also report the results with a 3-dimensional solids rendering plot. In one embodiment of a quality assurance testing application, the processor 110 displays details to particular manufacturing tolerances that the pipe 140 fails to meet. Although several techniques to output the results are described above, skilled artisans will realize that other output methods may be used in place of or in combination with the above techniques.

Figure 6A:
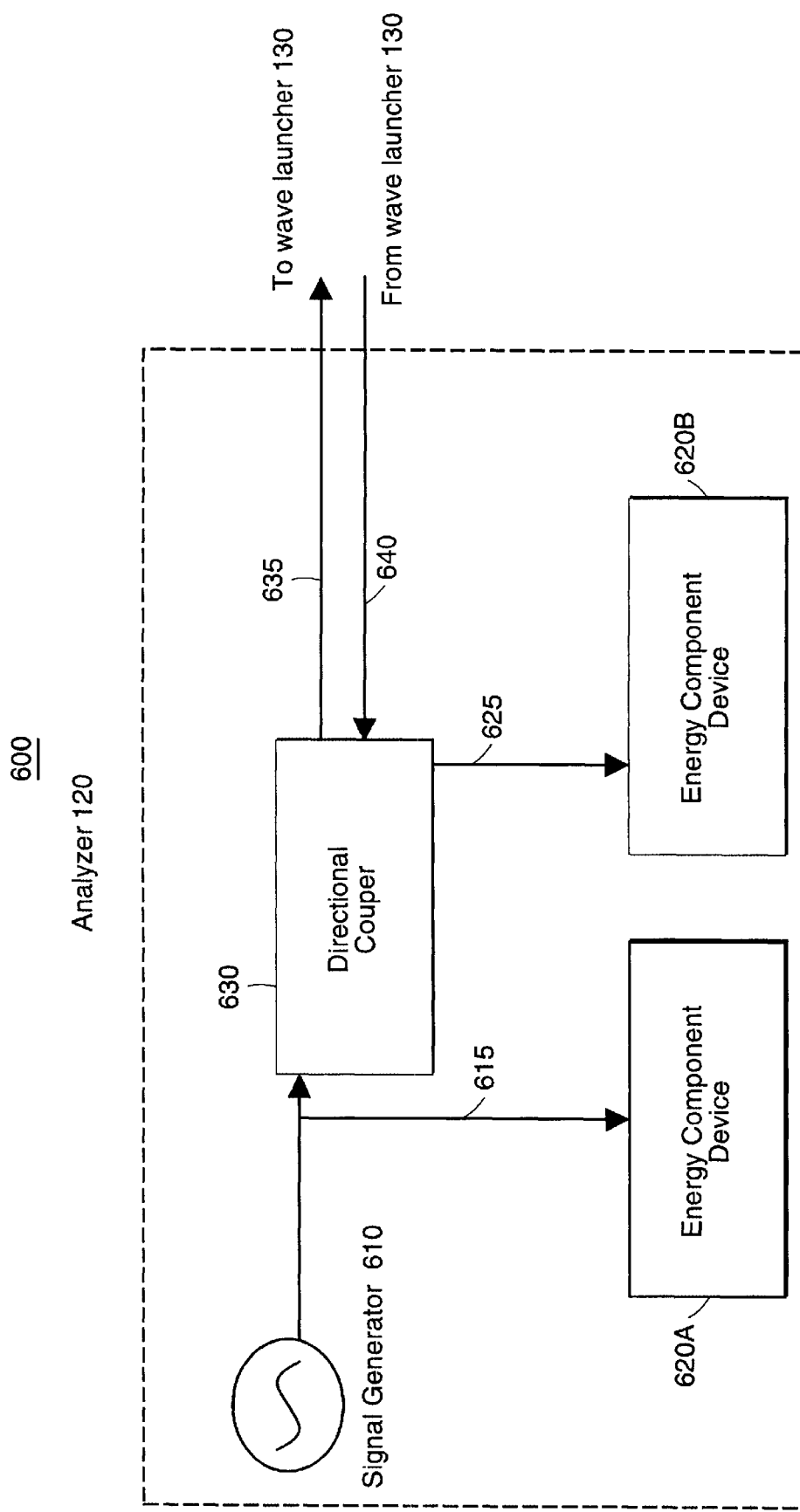
FIG. 6A is a conceptual block diagram depicting the illustrative analyzer of FIG. 1A.

FIG. 6A is a more detailed block diagram 600 of the illustrative analyzer 120 of FIG. 1A. In one embodiment, the analyzer 120 is an automated vector network analyzer. More specifically, the analyzer 120 is, for instance, an HP8714 automated vector network analyzer, manufactured by Hewlett Packard of Palo Alto, Calif. The analyzer 120 includes a signal generator 610, energy component devices 620A and 620B, and a directional coupler 630. The directional coupler 630 transmits an input energy 615 associated with the input waveform 235 to the energy component device 620A. The directional coupler 630 transmits a reflected energy 625 associated with the reflected component 245 to the energy component device 620B. The directional coupler 630 transmits the input waveforms 235 to the wave launcher 130 along a first communication channel 635. The wave launcher 130 transmits the reflected component 245 of the input waveform 235 to the analyzer 120, and more specifically to the directional coupler 630, along a second communication channel 640.

The signal generator 610 generates the input waveform 235 that is transmitted along the pipe 140. The signal generator 610 generates input waveforms 235 having a frequency within a certain range of frequencies, determined by the characteristics of the signal generator 610 and by the characteristics of the pipe 140. As described above, the pipe 140 acts as a waveguide for the input waveform 235, and input electromagnetic waveforms 235 propagate along a waveguide with different field configurations (e.g., electric field and magnetic field) and different velocities. This is referred to as the mode of the wave, and different modes of a wave can propagate along a waveguide simultaneously.

The energy component devices 620A, 620B extract out the magnitude and phase components of the input energy 615 and the reflected energy 625 associated with the input waveform 235 and the reflected component 245, respectively. The processor 110 requires the magnitude and phase of the input energy 615 and the reflected energy 625 to determine the attributes of the anomaly 150. The energy component devices 620A and 620B do not affect the input waveform 235, the reflected component 245, the input energy 615, or the reflected energy 625 when extracting out the magnitude and phase of the input energy 615 and the reflected energy 625.

The directional coupler 630 transmits and receives energy between the signal generator 610, the energy component device 620B, and the wave launcher 130 without any physical connection between the devices. In one embodiment, the directional coupler 630 uses the electric fields generated by the circuits of these components to transmit and receive energy.

Figure 6B:
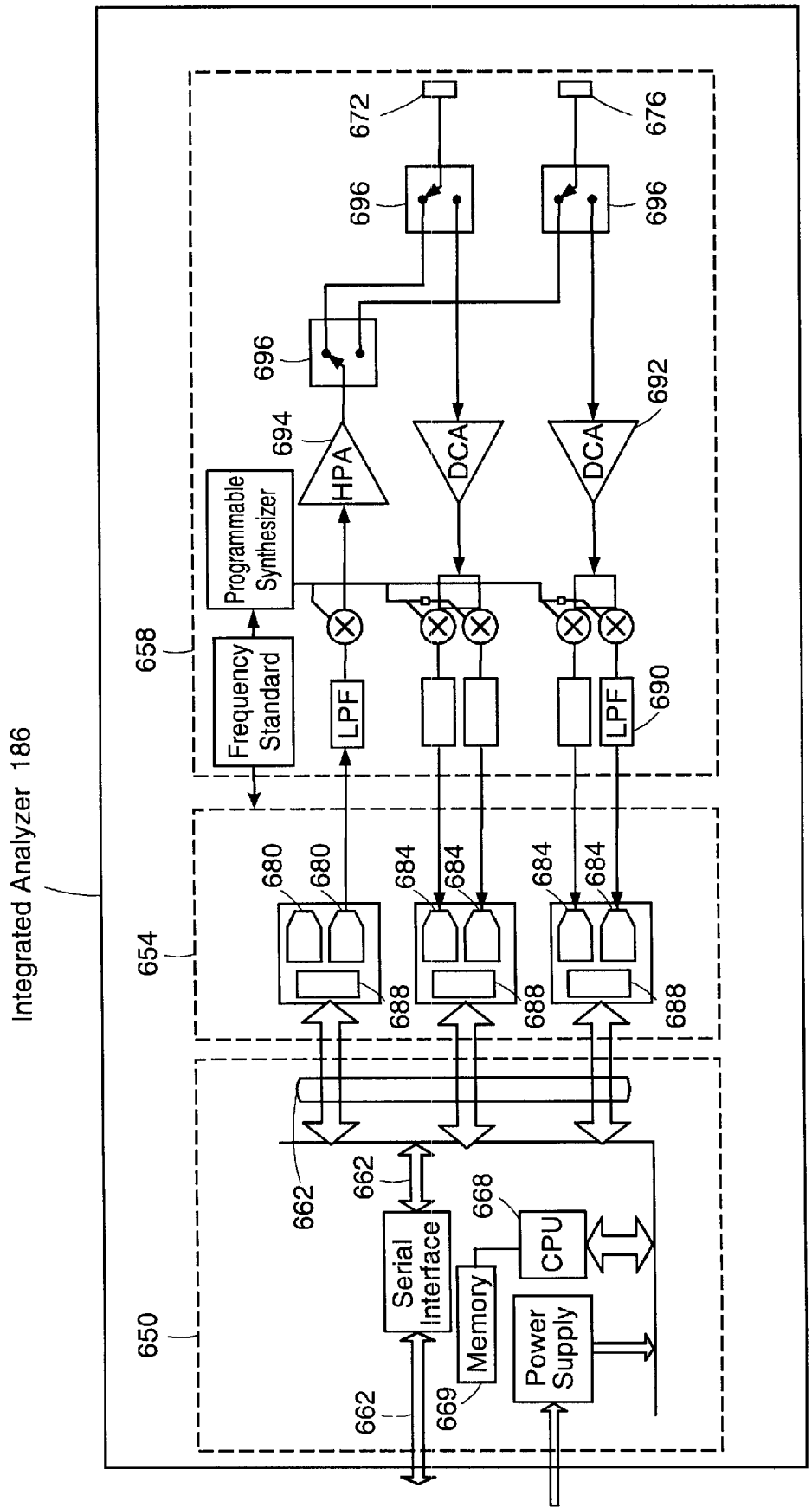
FIG. 6B is a conceptual block diagram of one implementation of the illustrative analyzer of FIG. 1B.

FIG. 6B illustrates a schematic block diagram of one implementation of the integrated analyzer 186. The integrated analyzer 186 includes a microsystem 650, a mixed-signal card 654, and a radio frequency (RF) subsystem 658. The microsystem 650 communicates with the pipe welding processor 180 (when the clamp 184 is removed) and the mixed-signal card 654. This communication occurs using any conventional means, such as with an integrated analyzer communications link 662. The microsystem 650 also includes an embedded central processing unit (CPU) 668 that transmits and receives commands from the pipe welding processor 180, collects measured data, and transmits the data to the pipe welding processor 180. The CPU 668 also includes local memory 669, such as random-access memory (RAM), to store the measured data.

The mixed-signal card 654 includes digital to analog converters (DACs) 680 and/or analog to digital converters (ADCs) 684 to enable transmission of an analog waveform and enable representation in a digital format by the microsystem 650. The mixed signal card 654 uses the DAC 680 to convert a digital input from the microsystem 650 to an analog input waveform 235 to be transmitted along the pipe 140. Likewise, the mixed signal card 654 uses the ADC 684 to convert an analog input from the integrated wave launcher 188 to a digital format for use by the microsystem 650. The mixed signal card 654 may also have memory 688, such as random-access memory (RAM), for storage of the data.

The RF subsystem 658 is adapted to transmit the generated input waveform 235 (not shown) to the integrated wave launcher 188 and is adapted to receive any and all reflected components 380 (not shown) from the integrated wave launcher 188. The RF subsystem 658 includes one or more low pass filters 690, a digitally-controlled amplifier (DCA) 692 and a high power amplifier (HPA) 694. The HPA 694 amplifies a waveform that the mixed-signal card 654 transmits to the RF subsystem 658. The DCA 692 provides low noise and high linearity (to avoid unwanted "mixing" of the multiple received signals being amplified. The DCA 692 amplifies the reflected components received from the integrated wave launcher 188. More specifically, the gain of the DCA is adjusted to make the optimum tradeoff between signal-to-noise ratio (requiring high gain) and linearity (requiring low gain). The RF subsystem 658 also includes one or more switches 696 to switch between a first port 672 and a second port 676. The ports 672, 675 provide an interface for a connection to the integrated analyzer 186.

As an example of the processor 110 employing the integrated analyzer 186 for pipe inspection use, the processor 110 communicates to the CPU 668 to inspect a pipe 140. The CPU 668 transmits a start command to the mixed-signal card 654 and the RF subsystem 658 to notify the components 654, 658 to prepare for the transmission of an input waveform 235. In another embodiment, the processor 110 transmits the start command to the mixed-signal card 654 and the RF subsystem 658 via the integrated analyzer communications link 662. The CPU 668 further configures the integrated analyzer 186 to transmit all input waveforms 235 to the integrated wave launcher 188 over the first port 672.

The CPU 668 then digitally generates a baseband waveform (i.e., a digital representation of the input waveform 235). The CPU 668 then transmits this digital signal to the DAC 692 of the mixed-signal card 654 over the integrated analyzer communications link 662 for conversion from the digital spectrum to an analog waveform. The DAC 680 additionally transmits this waveform to the HPA 694 for amplification of the signal strength of the input waveform 235. The HPA 694 then transmits the input waveform 235 to the integrated wave launcher 188 via the first port 672 for subsequent transmission along the pipe 140.

Once the transmission of the input waveform 235 is complete, the RF subsystem 658 enables a "receive mode" of the RF subsystem 658 to receive all transmissions from the integrated wave launcher 188. For example, the RF subsystem 658 enables the second port 676 to receive these transmissions. Moreover, the RF subsystem 658 may disable any transmission following the transmission of the input waveform 235 by disabling the first port 672. Alternatively, the RF subsystem includes a timer (not shown) that configures the switches 696 to a "receive mode" that disables the first port 672 following a predetermined amount of time. In further embodiments, the RF subsystem 658 triggers the timer once the RF subsystem 658 receives the start command from the CPU 668.

In response to receiving data from the integrated wave launcher 188 (e.g., the reflected component 245), the RF subsystem 658 transmits the analog data to the mixed-signal card 654. The ADC 684 converts the analog data to a digital format and transmits an interrupt over the integrated analyzer communications link 662 to interrupt the normal processing of the CPU 668. After interrupting the CPU 668, the ADC 684 transmits the data to the CPU 668. The CPU 668 then copies the data into its local memory 669 for storage. The integrated analyzer 186 repeats the above sequence for all data that the integrated wave launcher 188 transmits to the integrated analyzer 186.

Once the integrated analyzer 186 receives all of the data from the integrated wave launcher 188, the CPU 668 retrieves all of the data that the CPU 668 had stored. The CPU 668 then transmits this data to the pipe welding processor 180 for logging, processing, interpretation, transmission, and/or display.

Figure 7:
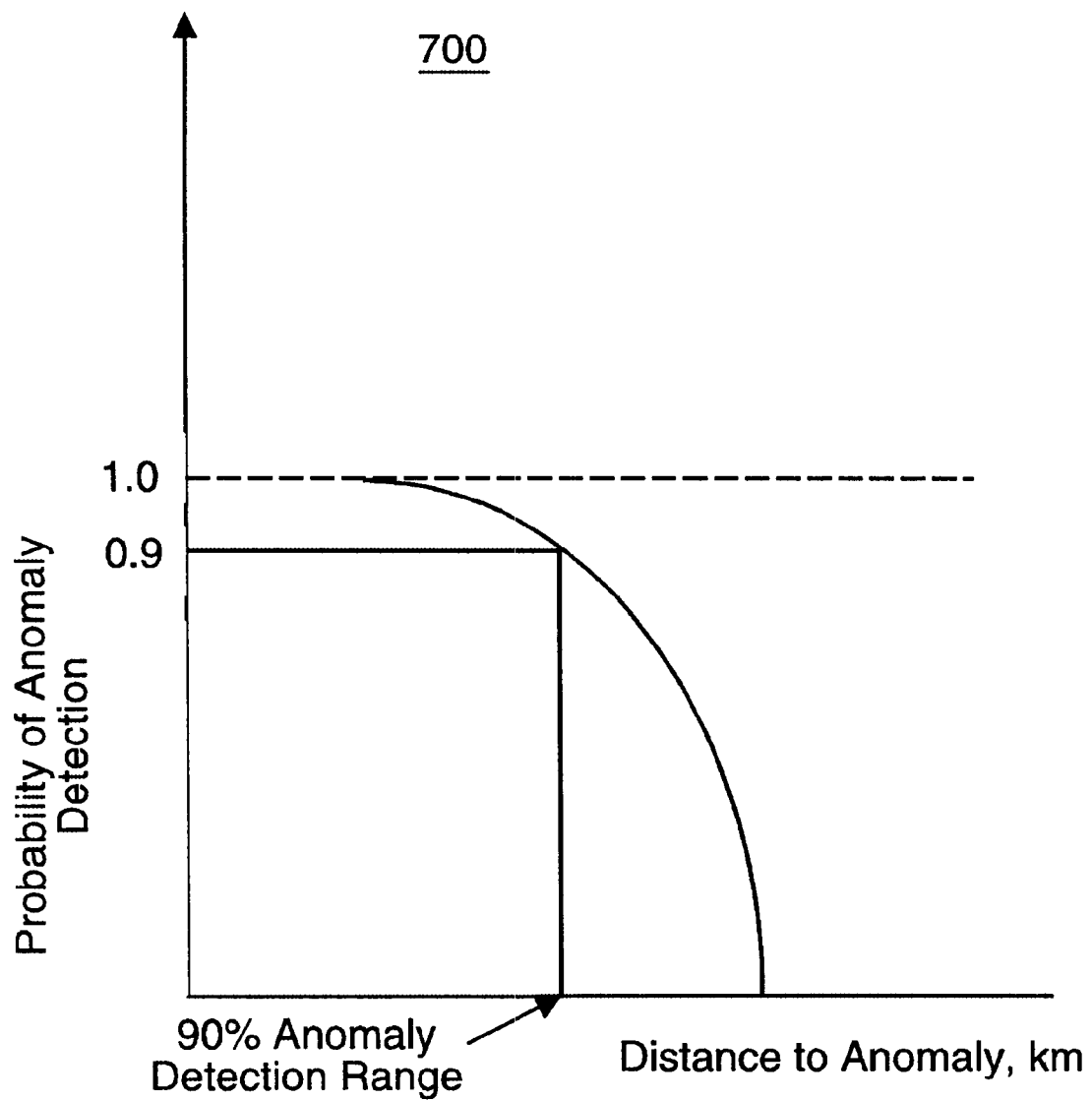
FIG. 7 depicts a graph describing a probability that a single anomaly will be detected using the illustrative system of FIGS. 1A and 1B as the distance between the anomaly and the wave launcher of FIGS. 1A and 1B increases.

FIG. 7 shows a graph 700 describing the probability that the inspection system 100, 175 detects the anomaly 150 as the distance 160 between the anomaly 150 and the wave launcher 130 increases. The graph 700 describes the probability that the inspection system 100, 175 detects the anomaly 150 in a straight pipe 140 or a curved pipe 140. For example, the graph 700 represents the probability that the inspection system 100, 175 detects the anomaly 150 in a straight pipe 140 when the input waveforms 235 propagate at particular frequencies, referred to below as the dominant mode of the input waveform 235. The graph 700 also represents the probability that the inspection system 100, 175 detects the anomaly 150 in a curved pipe 140 when the input waveforms 235 propagate at frequencies corresponding to more than one mode of the input waveform 235.

Figure 8:
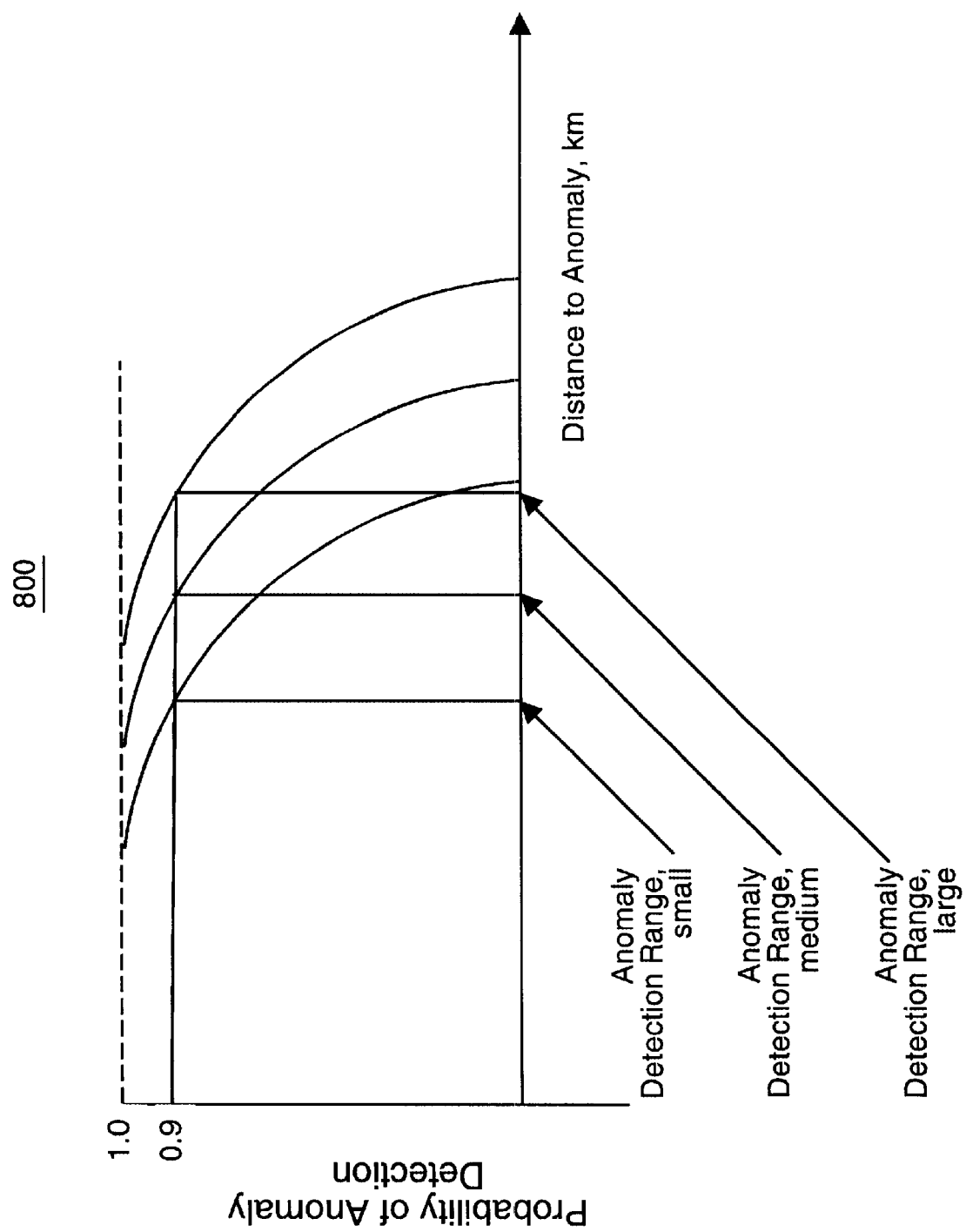
FIG. 8 is a graph describing a probability that a single anomaly of varied sizes (small, medium, large) will be detected using the illustrative system of FIGS. 1A and 1B as the distance between the anomaly and the wave launcher increases.

FIG. 8 is a graph 800 illustrating the probability that the inspection system 100, 175 detects a single anomaly 150 as the size (e.g., small, medium, large) of the anomaly 150 varies. The amplitude of the reflected component 245 increases as the size of the anomaly 150 increases. Therefore, the probability of detection generally increases as the size of the anomaly 150 increases. This increase is represented by translating the left curve shown in FIG. 8 to the right as the size of the anomaly 150 increases.

In greater detail about the pipe 140 and the input waveform 235 and referring again to FIGS. 1A, 1B, and 6, the pipe 140 has a cutoff frequency below which no input waveform 235 propagates. This cutoff frequency is the minimum frequency needed to propagate the first mode of the input waveform 235 along the pipe 140. The first mode of an electromagnetic waveform, which propagates along the pipe 140 alone, is called the dominant mode of the waveguide. The minimum frequency at which the dominant mode exists, which is the cutoff frequency, depends on the cross-section 144 of the opening of the pipe 140. The maximum frequency at which the dominant mode exists depends on the characteristics of the pipe 140.

In one embodiment, the pipe 140 is a substantially circular cylindrical pipe 140, and the range of frequencies at which the dominant mode propagates is given by the following relationship:

$$\frac{K_1 c}{a} < f_d < \frac{K_2 c}{a}$$

wherein:

$f_d$ is the frequency at which the dominant mode propagates along the pipe 140;

c is the speed of light ($2.998 \times 10^8$ meters/second);

$K_1$ and $K_2$ are constants associated with the characteristics of the pipe 140; and $\alpha$ is the radius of the circular cross-section 144 of the pipe 140.

For a circular cylindrical pipe 140, the dominant mode is referred to as the $TE_{11}$ mode. TE waves are waves in which the longitudinal components of the electric field at the walls of the waveguide are zero and the longitudinal magnetic field is non-zero. In one embodiment, the signal generator 610 transmits the dominant mode of the input waveform 235. The illustrative signal generator 610 generates an input waveform 235 for the entire range of frequencies at which the dominant mode exists. When the input waveform 235 is at a frequency associated with the dominant mode, the analyzer 120 generates a unique transfer function relating the input energy 615 and the reflected energy 625. The transfer function is unique because the dominant mode is the only mode of the input waveform 235 that propagates along the pipe 140.

According to one illustrative embodiment of the invention, the user of the inspection system 100, 175 enters the diameter information of the pipe 140 into the processor 110. According to another embodiment, the user enters the shape and dimensions of the cross-section 144 of the pipe 140 into the processor 110. The processor 110 uses the entered information to determine the frequency range at which the dominant mode of the input waveform 235 propagates. The processor 110 then notifies the analyzer 120 to generate input waveforms 235 each having a frequency within the range of frequencies of the dominant mode. Alternatively, the user of the inspection system 100, 175 enters the brand name of the pipe 140 and the processor 110 uses this data to retrieve from its local memory the cross-sectional information of the pipe 140. Generally, the user of the inspection system 100, 175 can input any parameter of the pipe 140 into the processor 110 as long as the processor 110 can determine the frequency range of the dominant mode of the pipe 140.

In one embodiment and as briefly described above with respect to FIG. 5, the analyzer 120 generates a chirp waveform as the input waveform 235. A chirp waveform is a quasi-sinusoidal waveform that has the property that its instantaneous frequency is a linear function of time. The analyzer 120 generates discrete chirp waveforms and increments the frequency of the input waveform 235 by a step-size through a range of sinusoidal frequencies. By way of example, the analyzer 120 generates discrete chirp waveforms and increments the frequency by a step-size of 1 Hz through 3 Hz (i.e., the analyzer 120 generates discrete chirp waveforms having a frequency of 600 MHz, 601 MHz, and 602 MHz).

In another embodiment and as briefly described above with respect to FIG. 5, the analyzer 120 generates a prototype waveform and derives a wavelet waveform as the input waveform 235. The analyzer 120 derives a wavelet waveform by stretching or delaying the prototype waveform. The analyzer 120 has a high degree of control over the joint time and frequency distribution of the input energy 615 in the wavelet waveform. For example, a wavelet waveform can be derived such that all frequency components arrive at substantially the same time and substantially in phase.

In another embodiment, the analyzer 120 generates a spread spectrum waveform as the input waveform 235. The spread spectrum waveform reduces interference by spreading the input waveform 235 in bandwidth prior to transmission along the pipe 140. Upon receiving the reflected component 245 of the input waveform 235, the analyzer 120 despreads, or decreases, the bandwidth of the reflected component 245 by the same amount of bandwidth as the increase. This technique in turn decreases the effect of the interference that occurs during the transmission and reception of the input waveform 235 and the reflected component 245.

When the wave launcher 130 launches many input waveforms 235 of different frequencies within the range of frequencies of the dominant mode, each input waveform 235 travels along the central axis 142 of the pipe 140 at different velocities due to the different frequencies. This is referred to as "dispersion" of the input waveform 235. When the pipe 140 is a relatively straight pipe 140, the operation of the inspection system 100, 175 is not affected by the different velocities of the input waveforms 235 because each input waveform 235 has a separate component 245 of the input waveform 235 reflected toward the wave launcher 130 at different times corresponding to the different velocities. Therefore, the inspection system 100, 175 detects the anomaly 150 when the input waveform 235 disperses in a straight pipe 140.

In another embodiment, the pipe 140 is a pipe 140 that has curves and bends. As previously described above, the user of the inspection system 100, 175 may provide information such as cross-sectional and axial curvature information to the processor 110. The processor 110 uses this information to calculate the range of frequencies corresponding to the dominant mode as well as the range of frequencies corresponding to higher order modes of the input waveform 235 and to generate a mathematical model of the pipe 140. Alternatively, the system 100, 175 determines the cross-sectional and axial curvature properties of the pipe 140. Either way, in one embodiment the signal generator 610 generates input waveforms 235 within a range of frequencies that correspond to more than one mode of the input waveform 235 (i.e., the dominant mode and higher order modes). The wave launcher 130 then launches these input waveforms 235 along the central axis 142 of the curved pipe 140. The analyzer 120 receives an independent reflected energy 625 along the second communication channel 640 for each input waveform 235 that was introduced.

In one embodiment and as described above, the processor 110 compensates for dispersion in its formulation of the model pipe and therefore forces time-alignment of all the frequencies of the input waveforms 235 that travel at different velocities. The pipe 140 incorporates dispersion into its DSP algorithms to model the pipe 140 because the dominant mode dispersion of an input waveform 235 is substantially identical in both a straight section 910 and a curved section 918 of the pipe 140. For example, the lossy physics-based model 425 described above compensates for dispersion. More specifically, the lossy physics-based model 425 described above incorporates dispersion in its formulation of the model pipe with the term under the second radical in Equation (5).

In another embodiment, the processor 110 uses the transfer function of each input waveform 235 to determine which model (ideal physics-based system model 400, average model, section-by-section model) of the pipe 140 to use. Therefore, the analyzer 120 helps the processor 110 accurately model the pipe 140 when the analyzer 120 generates higher order mode input waveforms 235 for a curved pipe 140 (e.g., second section 918).

The processor 110 models the curves in a pipe 140 more realistically as the number of modes that are propagating increases because of dispersion, which was described above. As the frequency of the input waveforms 235 increases, and therefore higher order modes propagate, the input waveforms 235 propagate around curves with greater differences in velocities relative to the difference in velocities along a relatively straight portion of the pipe 140. The processor 110 models the curves more accurately due to these velocity differences. Therefore, the inspection system 100, 175 detects the anomaly 150 when the pipe 140 is a curved pipe 140.

In another embodiment and as briefly described above with respect to FIG. 5, the analyzer 120 generates a soliton waveform as the input waveform 235. A soliton waveform is a class of waveforms designed to pass through a nonlinear dispersive media without losing its shape and properties. The processor 110 uses soliton waveforms as the input waveform 235 to characterize the curvature of the pipe 140. In one illustrative approach, the processor 110 determines the curvature of the pipe 140 by refining the shape of the soliton waveform in real-time until the analyzer 120 receives an unchanged reflected component 245. Alternatively, the processor 110 refines the spectral content of the soliton waveform in real-time until the analyzer 120 receives an unchanged reflected component 245. In another embodiment, the processor 110 refines the power level of the soliton waveform in real-time until the analyzer 120 receives an unchanged reflected component 245.

In another embodiment, the pipe 140 is a hollow rectangular pipe 140, and the dominant mode of the input waveform 235 propagates over the range of frequencies given by the following relationship:

$$\frac{c}{2a} < f_d < \frac{c}{2b}$$

wherein:
$f_d$ is the frequency at which the dominant mode will propagate along the rectangular pipe 140;
c is the speed of light ($2.998 \times 10^8$ meters/second);
α is the height of the pipe 140; and
b is the width of the pipe 140, assuming the width is less than the height of the pipe 140.

According to this embodiment, the user of the inspection system 100, 175 provides the processor 110 with the height and width of the pipe 140. With these parameters, the processor 110 determines the range of frequencies at which the dominant mode and higher order modes of the input waveform 235 propagate along the hollow rectangular pipe 140.

According to a further embodiment, the inspection system 100, 175 detects the axial curvature of the pipe 140 with or without an anomaly 150. As described above, the wave launcher 130 launches input waveforms 235 corresponding to the dominant mode and higher order modes of the input waveforms 235 along the central axis 142 of the pipe 140.

The axial curvature of the pipe 140 may be useful to the user of the inspection system 100, 175 for a variety of reasons. By way of example, it can be useful to determine a change in the degree of curvature over a period of time and to locate the end wall of the pipe 140 when the end wall is not located at the expected location, and the like. The change in the degree of curvature over a period of time also shows, for instance, a portion of the pipe 140 experiencing a greater amount of force applied to it relative to less curved portions. The user can use the curvature information to adjust characteristics of the pipe 140 such as re-position the pipe 140 in a modified location, pad the curved portion of the pipe 140 to adjust (i.e., decrease) the amount of force applied to it, apply a similar force to the uncurved portions of the pipe 140 to decrease the rate of curvature change along the pipe 140, or the like. In yet another embodiment, knowing an initial location point along the pipe 140 and curvature information determined by the inspection system 100, 175, a user of the inspection system 100, 175 can map the location of a length of pipe 140, even if the pipe 140 is underground or submerged underwater.

The location of any point along the pipe 140, such as the point corresponding to the end wall of the pipe 140, may be useful to the user of the inspection system 100, 175 for a variety of reasons. For example, a user of the inspection system 100, 175 may know the location of a point along the pipe 140 but may not know the location of the end wall of the pipe 140 if the pipe 140 is laid underground or underwater. Similarly, although a user of the inspection system 100, 175 may know the starting point of an old pipe 140 buried in the foundation of a building, a user may not know the path the pipe 140 takes throughout the foundation. One skilled in the art will appreciate that knowing the location of an entire segment of pipe 140 may, for example, aid in repair of an anomaly 150. Such information may also be helpful with regard to installing additional pipe 140 segments.

Figure 9A:
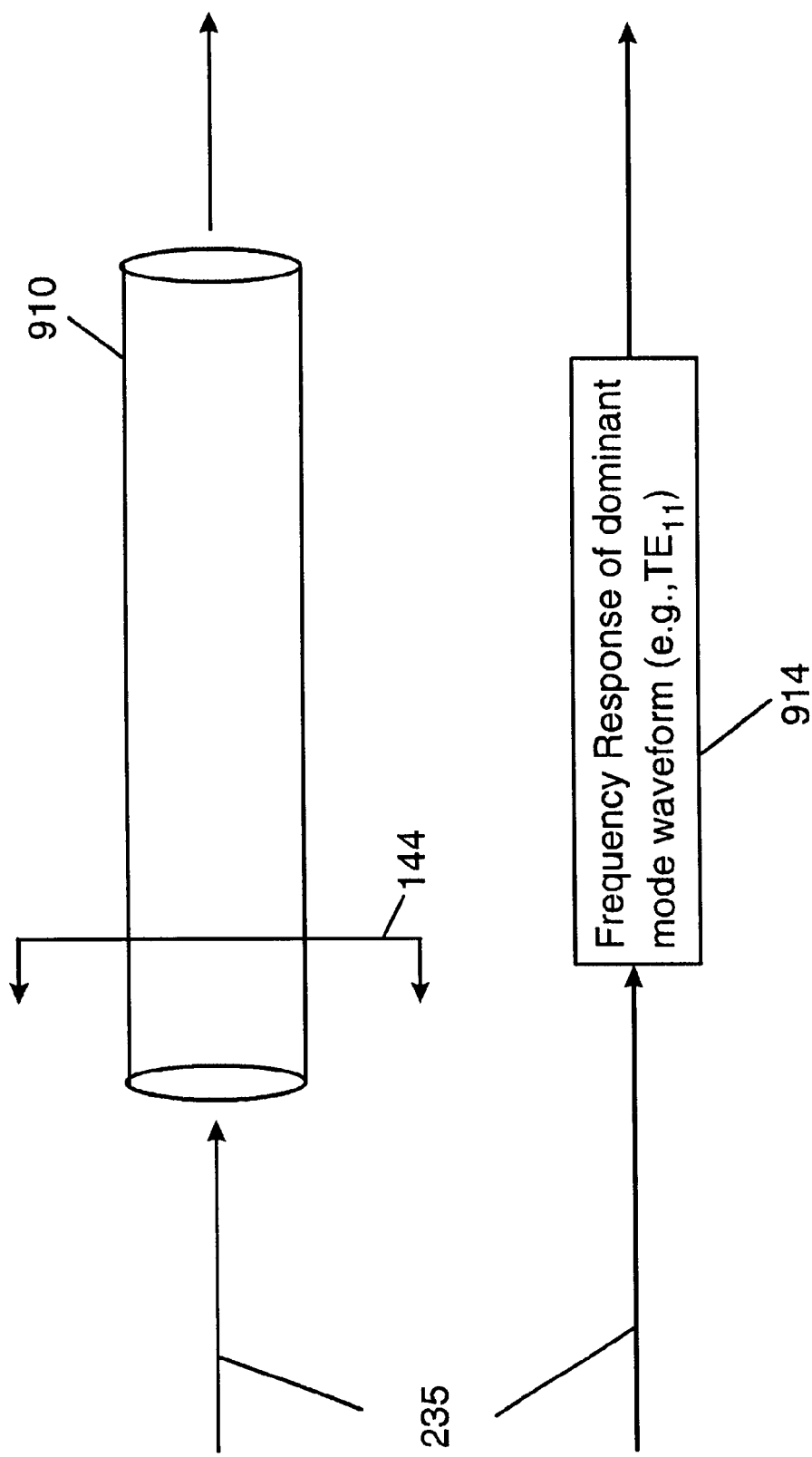
FIG. 9A is a conceptual diagram depicting a modeled frequency response for an exemplary section of a pipe along which a dominant mode waveform is transmitted.

As an example and also referring to FIG. 9A, the processor 110 transmits the dominant mode of the input waveform 235 along a first section 910 of the pipe 140. The analyzer 120 determines the frequency response 914, or transfer function described above, of the first section 910 of the pipe 140. In one embodiment and as used herein, the first section 910 is a straight section of the pipe 140. By transmitting the dominant mode along the first section 910, the processor 110 determines the delay and attenuation of the input waveform 235 for each frequency within the range of frequencies at which the dominant mode exists. As generally known by those skilled in the art, the attenuation of the input waveform 235 is the decrease in intensity of the input waveform 235. Thus, as stated above, the frequency response 914 (i.e., the transfer function) of the input waveform 235 is unique when the analyzer 120 generates an input waveform 235 having a frequency associated with the dominant mode.

Figure 9B:
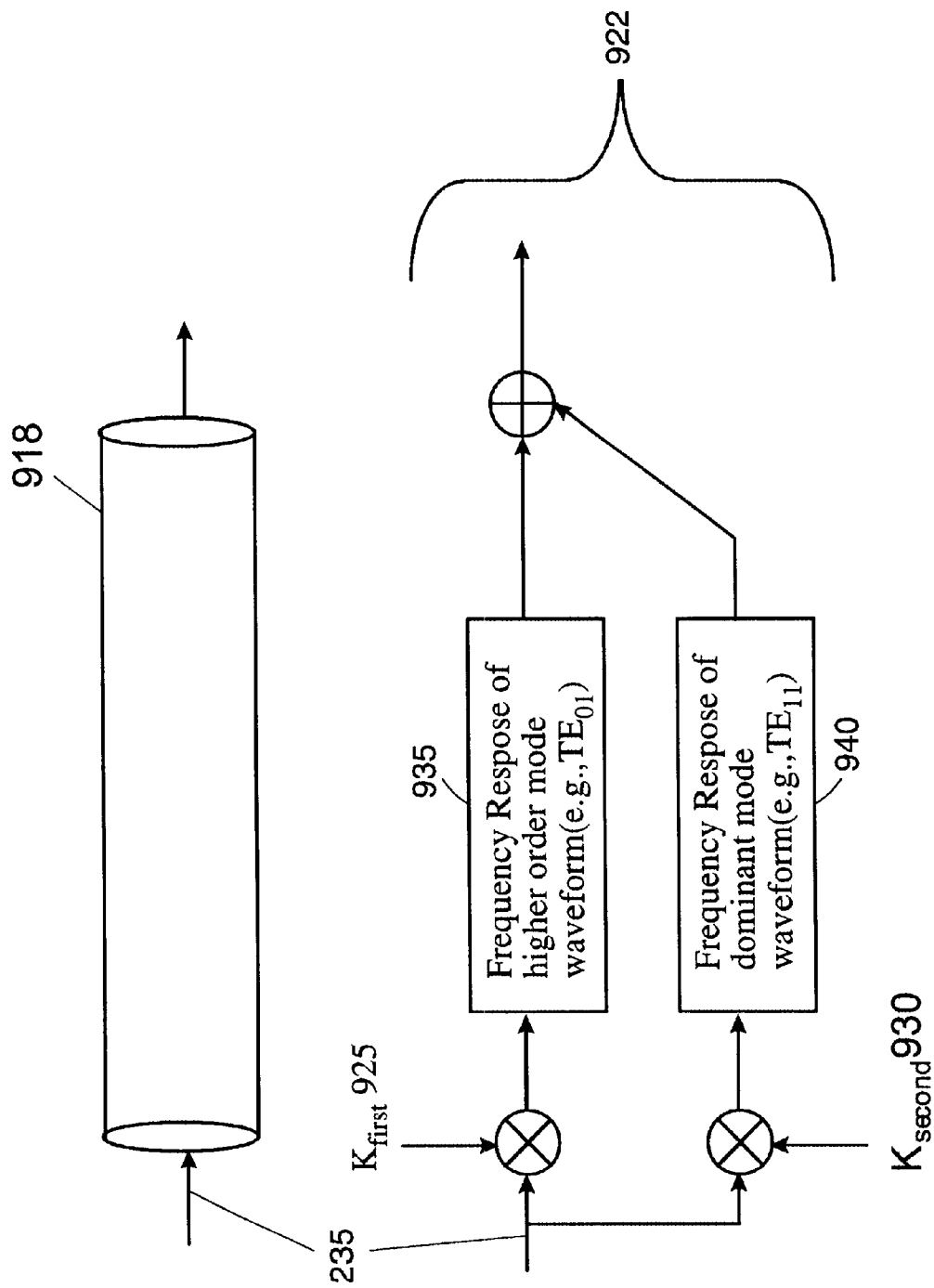
FIG. 9B is a conceptual diagram illustrating a modeled frequency response for an exemplary section of a pipe along which a higher order mode waveform is transmitted.

In greater detail and as illustrated in FIG. 9B, the inspection system 100, 175 can be used to determine the curvature of a second section 918 of the pipe 140. As noted above, contrary to the dominant mode (e.g., $TE_{11}$) of the input waveform 235, a higher order mode (e.g., $TE_{01}$) of the input waveform 235 that propagates along the pipe 140 does not exhibit a unique frequency response. Therefore, due to dispersion, a portion of the energy of the input waveform 235 becomes a dominant mode waveform (e.g., $TE_{11}$) when the pipe 140 curves. Similarly, a portion of the frequency response represents the dominant mode of the input waveform 235.

As shown in FIG. 9B and as noted above, the processor 110 (not shown) determines the curvature of the second section 918 of the pipe 140 using a first curvature detection model 922. The first curvature detection model 922 includes a first constant 925, also referred to as $K_{first}$, and a second constant 930, also referred to as $K_{second}$. The constants 925, 930 are constants associated with the characteristics of the second section 918 of the pipe 140. The first constant 925 is an input to a higher order mode frequency response 935. Similarly, the second constant 930 is an input to a dominant mode frequency response 940.

In one embodiment in which the pipe 140 curves, $K_{first}$ and $K_{second}$ are constants that represent the distribution of the energy between a straight section 910 and a curved section 918 of the pipe 140 for the dominant mode input waveform 235 and the higher order mode input waveform 235. In one embodiment, the processor 110 applies the first constant 925 to the higher order mode frequency response 935 (associated with higher order mode of the input waveform 235). Further, the processor 110 applies the second constant 930 to the dominant mode frequency response 940 (associated with the dominant mode of the input waveform 235). For example, if the section 918 of the pipe 140 is straight (e.g., the first section 910), then $K_{first}$ (and therefore the higher order mode frequency response 935) equals zero because the section 918 of the pipe 140 has no curvature. $K_{second}$ (and therefore the dominant mode frequency response 940) equals unity. This example illustrates the frequency response 914 of FIG. 9A.

As the radius of curvature of the second section 918 varies, the value of $K_{first}$ and/or $K_{second}$ also varies. Thus, the processor 110 varies the values of the constants 925, 930 to accurately model the curvature of the section 918 of the pipe 140.

Figure 10A:
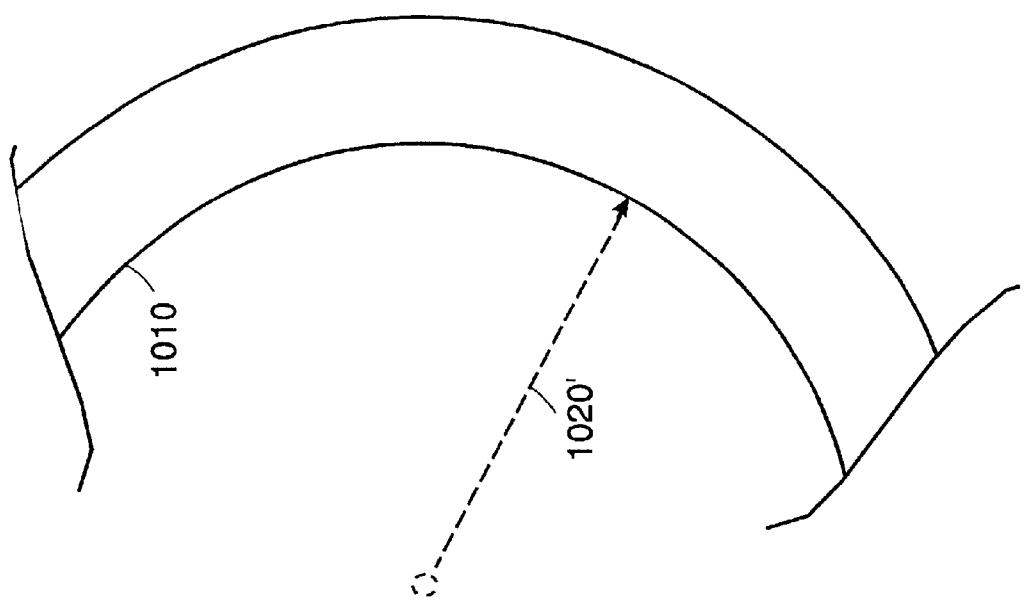
FIG. 10A depicts side-views of two curved pipe sections.
Figure 10A:
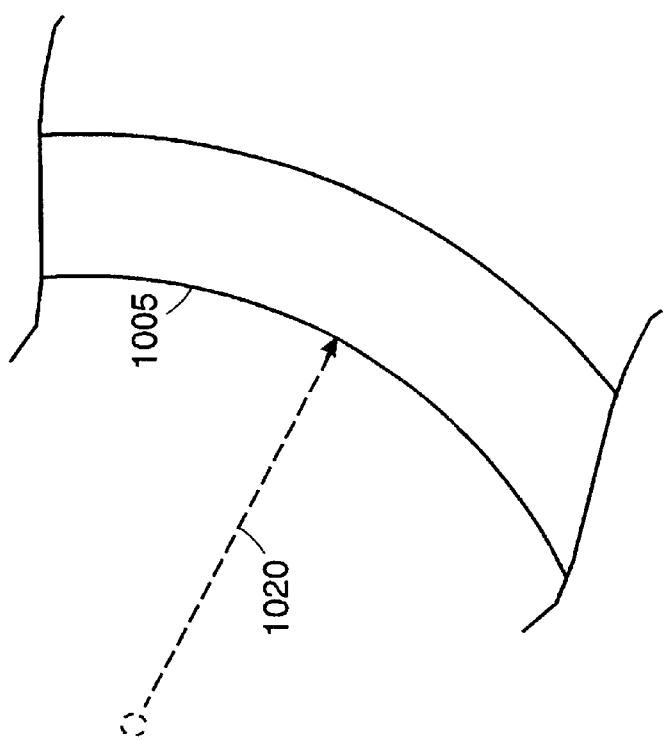

FIG. 10A illustrates exemplary side-views of a first curved section 1005 and a second curved section 1010 of the pipe 140. In the embodiment shown in FIG. 10A, the length of the first section 1005 is different than the length of the second section 1010. However, the radius 1020 of the first section 1005 is equivalent to the radius 1020' of the second section 1010.

Because the radii 1020, 1020' (generally 1020) are equivalent and also because the first constant 925 and the second constant 930 vary based on the radius of the section 1005, 1010 of the pipe 140, the processor 110 cannot accurately model the first section 1005 and the second section 1010 of the pipe 140 using the first curvature detection model 922.

Figure 10B:
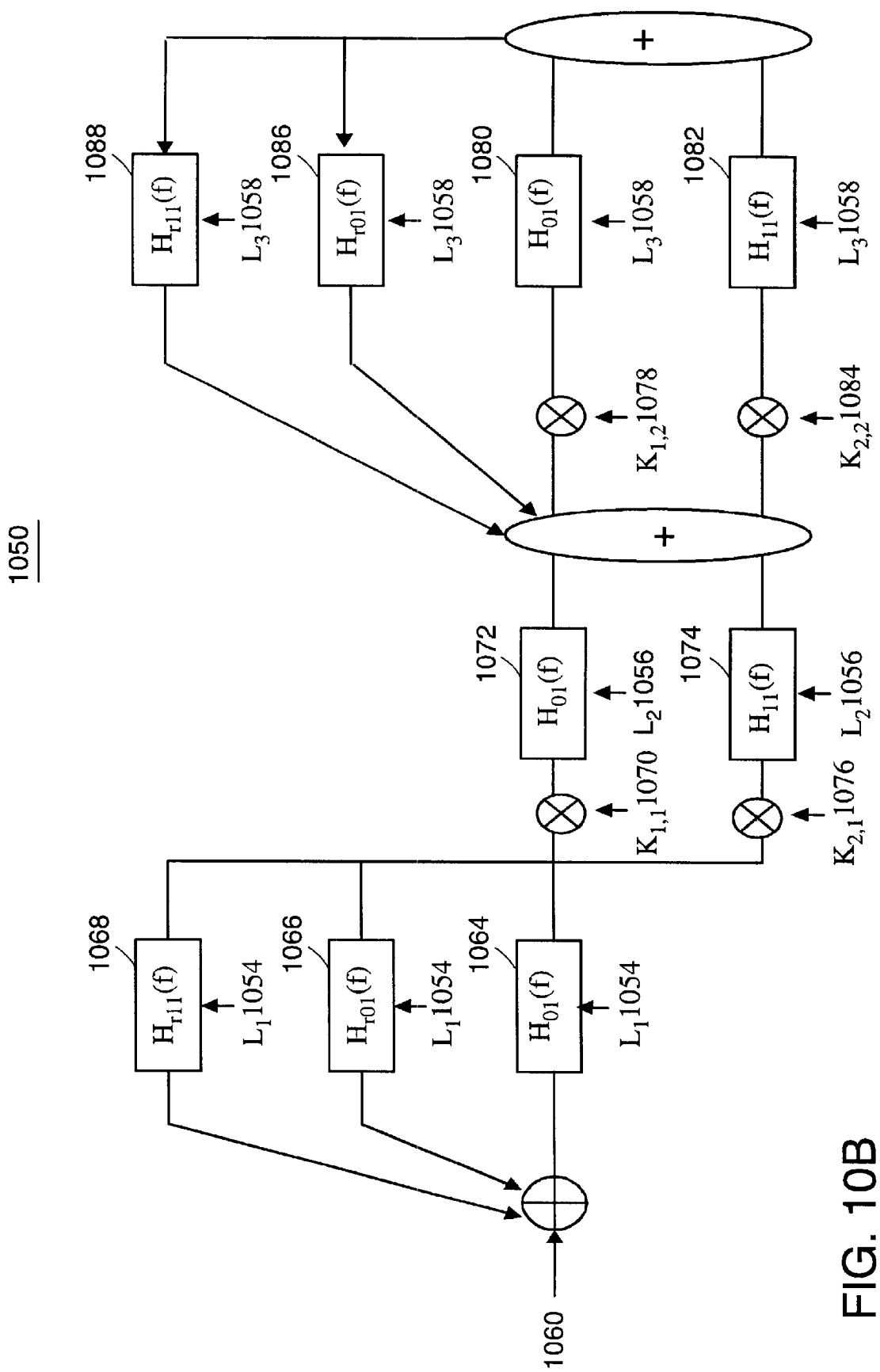
FIG. 10B is a conceptual diagram depicting a modeled frequency response for a curved section of pipe, according to an illustrative embodiment of the invention.

Referring to FIG. 10B, the processor 110 instead employs a second curvature detection model 1050 to determine the curvature of the first section 1005 and the second section 1010 of the pipe 140 having equivalent radii 1020 but different lengths. In the embodiment shown, the processor 110 models each section 1005, 1010 of the pipe 140 as smaller sections having a length that is less than the radius 1020 of the section 1005, 1010 of the pipe 140. For example and as shown in FIG. 10B, the processor 110 models the first section 1005 and/or the section 1010 of the pipe 140 as three sub-sections: a first sub-section having a first length $L_1$ 1054, a second sub-section having a second length $L_2$ 1056, and a third sub-section having a third length $L_3$ 1058.

To accurately model the section 1005, 1010 of the pipe 140, the processor 110 inputs a higher order mode (e.g., $TE_{01}$) model waveform 1060 to the model 1050. The model 1050, with respect to the first sub-section, represents the frequency response of the higher order model waveform 1060 as $H_{01}(f)$ 1064. As each section 1005, 1010 includes curves, after the model waveform 1060 passes the first length $L_1$ 1054, the model waveform 1060 reflects a higher order mode component 1066 (shown in FIG. 10B as $H_{r01}(f)$ 1066) and also reflects a dominant mode component 1068 (shown in FIG. 10B as $H_{r11}(f)$ 1068) toward the analyzer 120.

Once the model waveform 1060 traverses the first length $L_1$ 1054, the processor 110 then multiplies the frequency response 1064 of the higher order mode model waveform 1060 with a first constant $K_{1,1}$ 1070 associated with the first length $L_1$ 1054. The first subscript of the constant represents the constant number (e.g., first constant, $K_1$) and the second subscript represents the length that the constant associates with (first length $L_1$, first constant $K_{1,1}$). The processor 110 models the higher order mode of the model waveform 1060 of the second sub-section with a second model higher order mode frequency response $H_{01}(f)$ 1072. Furthermore, and as shown above in FIG. 9B, the input waveform 235 produces a dominant mode waveform when the section of the pipe 140 is curved. Consequently, the processor 110 models this dominant mode portion of the model input waveform 1060 produced between the first length $L_1$ 1054 and the second length $L_2$ 1056 with a dominant mode frequency response $H_{11}(f)$ 1074. The processor 110 also multiplies the frequency response 1074 of the dominant mode model waveform 1060 with a second constant $K_{2,1}$ 1076 associated with the first length $L_1$ 1054.

At a point on the section 1005, 1010 of the pipe 140 that is equivalent to the second length $L_2$, the processor 110 multiplies the second model higher order mode frequency response 1072 with a first constant $K_{1,2}$ 1078 associated with the second length $L_2$ 1056. The processor 110 models the higher order mode of the model waveform 1060 of the third sub-section with a third model higher order mode frequency response $H_{01}(f)$ 1080. The processor 110 models the dominant mode portion of the model input waveform 1060 propagating between the second length $L_2$ 1056 and the third length $L_3$ 1058 with a second dominant mode frequency response $H_{11}(f)$ 1082. The processor 110 also multiplies the dominant mode frequency response 1082 with a second constant $K_{2,2}$ 1084 associated with the second length $L_2$ 1056.

The processor 110 models the section 1005, 1010 of the pipe 140 between the first length $L_1$ 1054 and the second length $L_2$ 1056 for the higher order mode of the model waveform 1060 by adjusting the first length $L_1$ 1054 and the second length $L_2$ 1056. The processor 110 then estimates the value of the first constant $K1,1$ 1070 associated with the first length $L_1$ 1054 and the value of the second constant $K_{1,2}$ 1078 associated with the second length $L_2$ 1056. In the same manner, the processor 110 also adjusts the value of the second constant $K_{2,1}$ 1076 associated with the first length $L_1$ 1054 and the value of the second constant $K_{2,2}$ 1084 associated with the second length $L_2$ 1056 to determine the lengths of the pipe 140 between the first and second lengths $L_1$ 1054 and $L_2$ 1056.

The processor 110 then communicates with the analyzer 120 and the wave launcher 130 to transmit an input waveform 235. The processor 110 consequently receives the reflected component 245 from the section 1005, 1010 of the pipe 140 and determines the actual values of the first constant $K_{1,1}$ 1070 and the second constant $K_{1,2}$ 1078 for a higher order mode of the model input waveform 1060. The processor 110 adjusts the value of the lengths $L_1$ 1054 and $L_2$ 1056 in the model 1050 until each of the adjacent constants (e.g., the first constant $K_{1,1}$ 1070 and the second constant $K_{1,2}$ 1078 and the first constant $K_{2,1}$ 1076 and the second constant $K_{2,2}$ 1084) converge to one value. When the constants converge, the model 1050 is accurate for that section 1005, 1010 of pipe 140.

For example, the processor 110 models a section 1005, 1010 of a pipe 140 by first determining to divide a model section into three sub-sections. The processor 110 creates the curvature detection model 1050 for the section. The processor 110 chooses a value for each constant K (i.e., $K_{1,1}$ 1070, $K_{1,2}$ 1078, $K_{2,1}$ 1076, $K_{2,2}$ 1084) and also chooses a value for each length of each sub-section (e.g., $L_1$ 1054, $L_2$ 1056, $L_3$ 1058). The wave launcher 130 then launches a higher order mode (e.g., $TE_{01}$) model waveform 1060 into the model 1050. The processor 110 subsequently compares the backscatter, which are the reflected frequency responses of the model input waveform 1060 (e.g., $H_{r01}(f)$ 1066, $H_{r11}(f)$ 1068, $H_{r11}(f)$ 1086, $H_{r11}$ 1088) with the backscatter associated with the input waveform 235 that the wave launcher 130 launches into the pipe 140 (i.e., the transfer function described above with respect to FIG. 2).

If the processor 110 determines the value of the measured first constant associated with the first length $L_1$ 1054 (which the processor 110 models with the first constant $K_{1,1}$ 1070) is large relative to the measured value of the adjacent second constant associated with the second length $L_2$ 1056 (which the processor 110 models with the second constant $K_{1,2}$ 1078), then the section of the pipe 140 that the processor 110 models in the model 1050 is straight between the first length $L_1$ 1054 and the second length $L_2$ 1056. In one embodiment, if the best estimates of the first constant $K_{1,1}$ 1070 and the second constant $K_{1,2}$ 1078 (made, for example, using the maximum likelihood procedure) shows that the former is much larger than the latter, then the processor 10 determines that little mode conversion has taken place. Therefore, the processor 110 determines that little curvature is present between the two lengths 1054, 1056.

In one embodiment, the processor 110 iteratively adjusts the values of the lengths and the constants of the model 1050 until the model 1050 accurately represents the section 1005, 1010. In another embodiment, the processor 110 optimizes the value of the lengths before comparing any value to a measured value. Thus, the processor 110 determines the geometry and curvature of the pipe 140 or a section 1005, 1010 of the pipe 140 using a model 1050 and transmitting a higher order model input waveform 1060 along the section 1005, 1010.

Figure 11A:
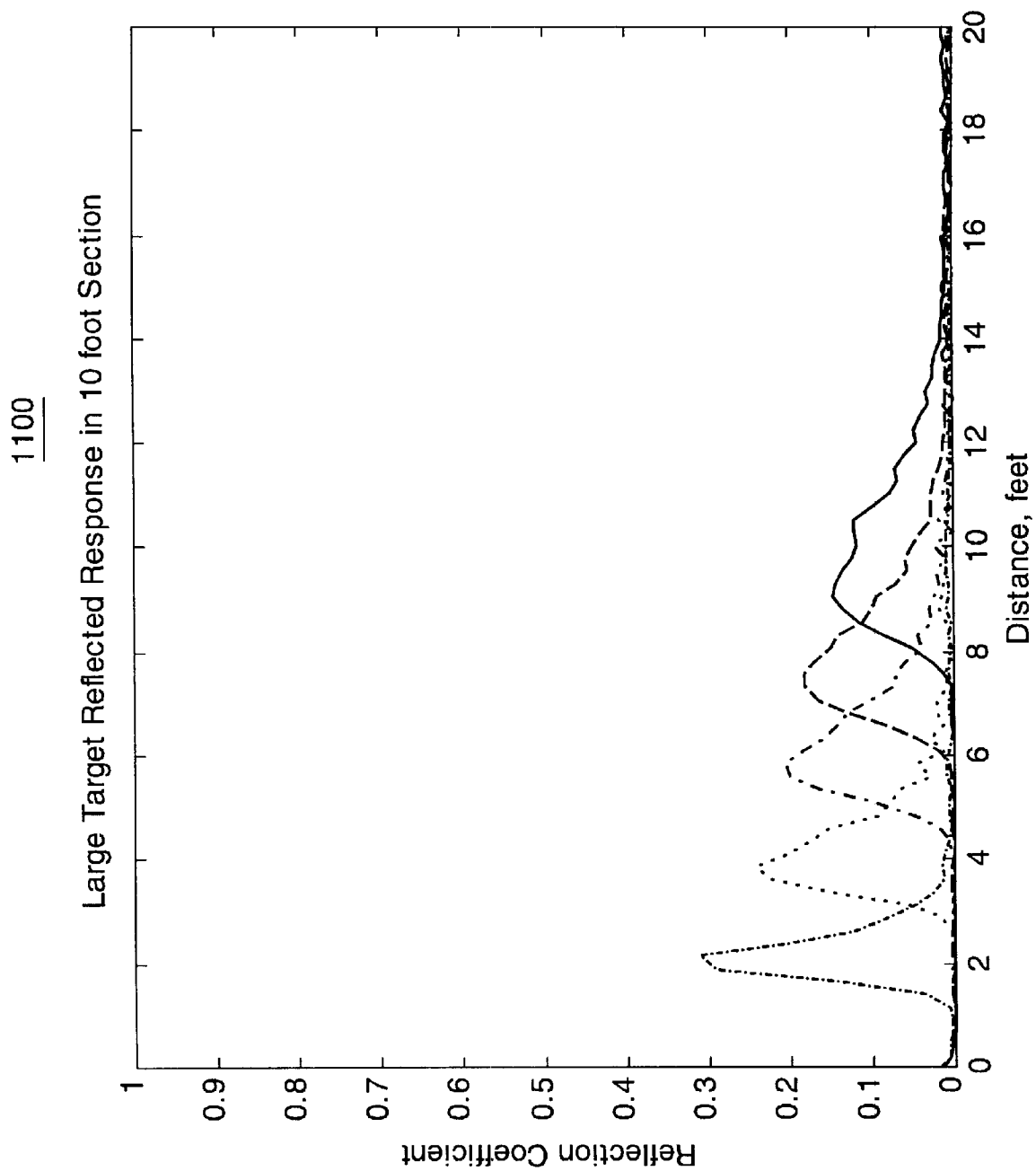
FIG. 11A is a graph describing an actual reflection response measured in a section of pipe as the distance along the section increases.

FIG. 11A is a graph 1100 describing an actual test reflection response of the reflected component 245 in a ten foot section (e.g., the first section 910) of the pipe 140 as a function of the distance along the section. Although described as a ten foot section, the invention extends to a section having any size. As can be seen in the graph, the reflection response depends on the reflection coefficient between the input waveform 235 and the reflected component 245. More specifically, the reflection coefficient is the ratio of the amplitude of the reflected component 245 and the amplitude of the input waveform 235. In a typical section of pipe, dispersion of an input waveform causes the reflection coefficient to decrease as the distance increases.

For example, the maximum reflection coefficient approximately equals 0.2 when the distance is approximately equivalent to 6 feet. When the distance increases to about 7.75 feet, the maximum reflection coefficient decreases to approximately 1.75 feet. Further, the sharpness of the curves decrease as the distance increases, illustrating the dispersion principle described above. In other words, the energy of an input waveform scatters as the distance increase because of dispersion.

Figure 11B:
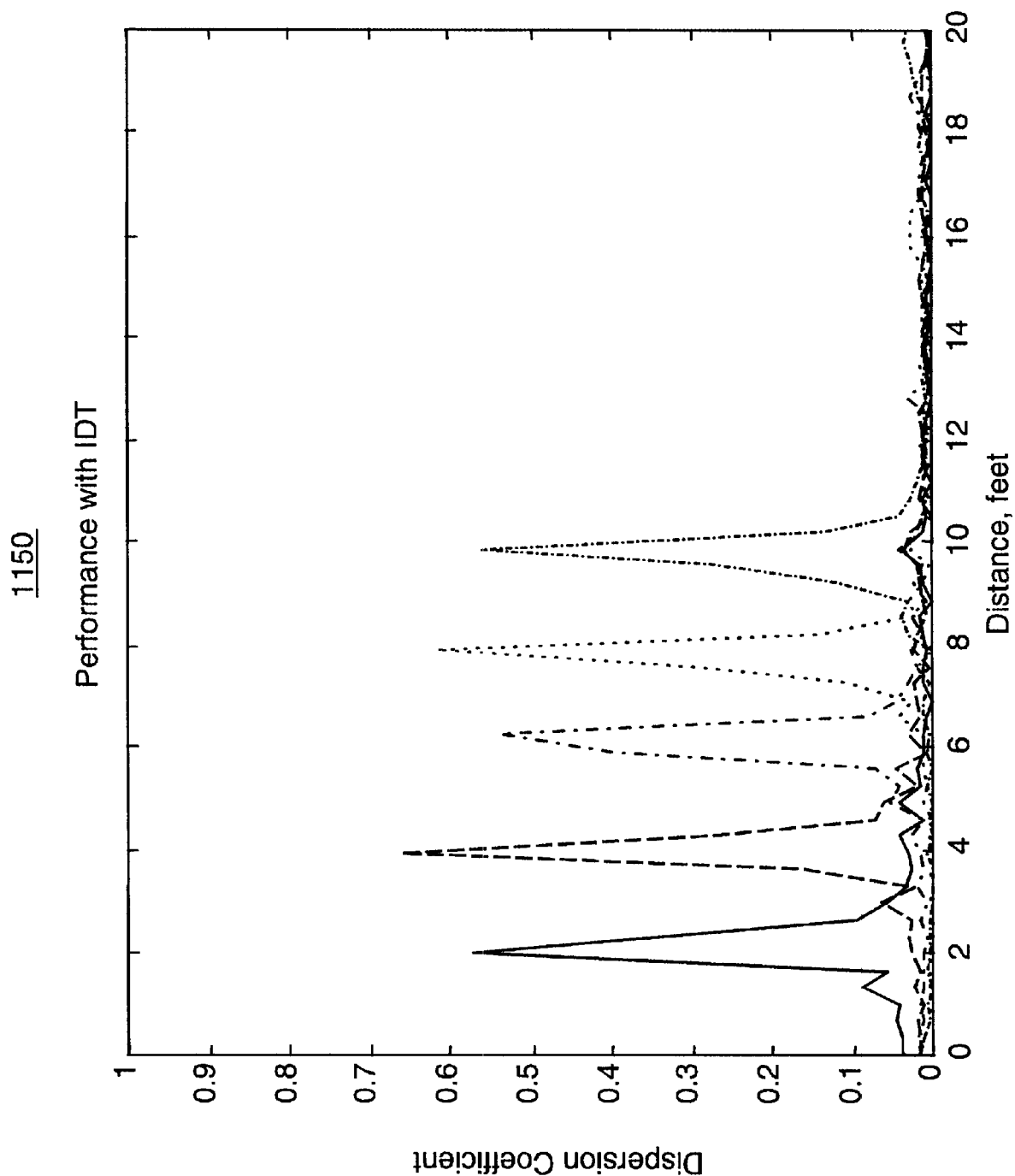
FIG. 11B depicts a graph describing an actual reflection response measured in a section of pipe as the distance along the section increases.

FIG. 11B is a graph 1150 depicting the dispersion coefficient as a function of distance when using the inspection system 100, 175 to collect actual test data. The graph 1150 illustrates the dispersion coefficient, which is obtained by processing the reflection coefficient through an inverse dispersion transform (IDT). The IDT breaks an input waveform up in a series of dispersive basis functions which are fundamental to the dispersion process generated by the pipe 140. The graph 1150 illustrates that the inspection system 100, 175 decreases the effects of dispersion shown above in FIG. 11A. Although dispersion of an input waveform typically causes the reflection coefficient to decrease as the distance increases, the inspection system 100, 175 lessens, and may even eliminate, this dispersion. This is shown by the sharpness of the curves—there is no decrease in the sharpness as the distance increases.

Figure 12:
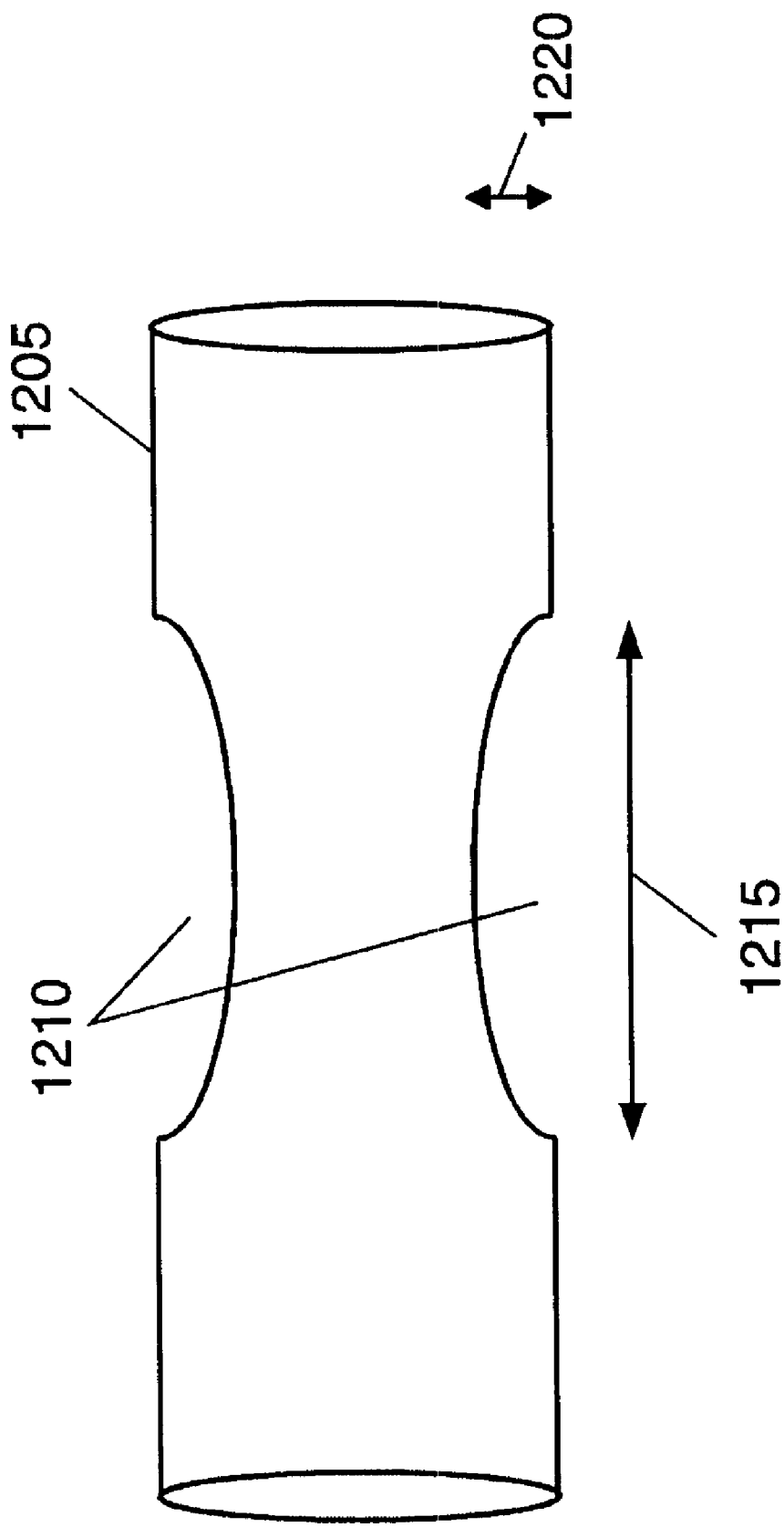
FIG. 12 is a conceptual diagram of an exemplary section of pipe having a deformity.

FIG. 12 is a conceptual diagram of a side-view of an exemplary section 1205 of the pipe 140 having a deformity 1210. The deformity 1210 can be any size and shape and can have any dimensions within the bounds of the pipe 140. Examples of causes of the deformity 1210 include, without limitation, a body of water exerting a higher amount of water pressure on the pipe relative to the limit of pressure that the pipe can handle, the section 1205 of the pipe experiencing a physical force on a region of the section 1205 that causes the deformity 1210, and the like. The deformity 1210 has a length 1215 and a thickness 1220 of the deformity 1210.

Figure 13:
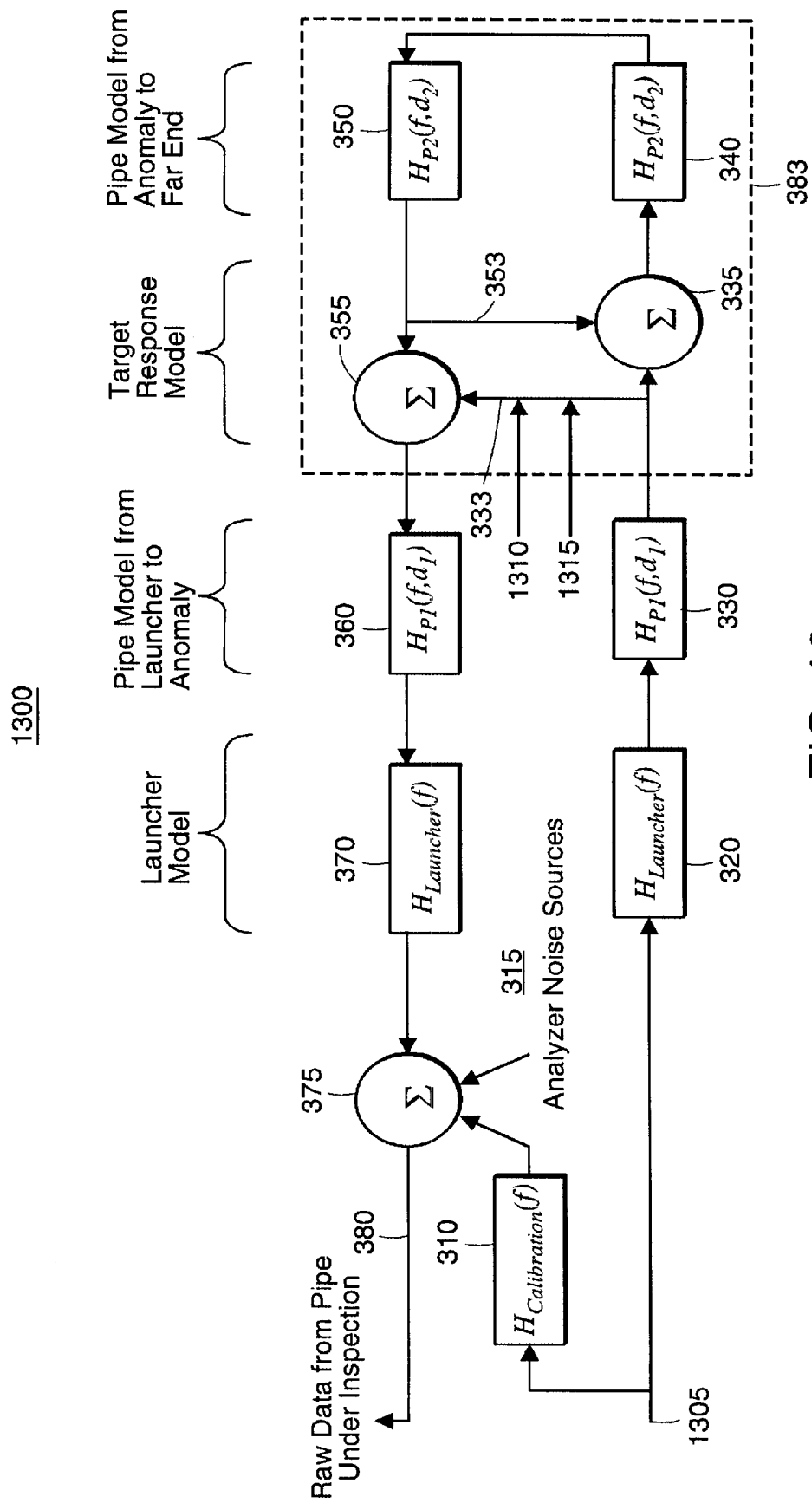
FIG. 13 is a conceptual diagram depicting a modeled frequency response for the pipe section of FIG. 12.

In one embodiment, the processor 110 models the section 1205 of the pipe 140 having the deformity 1210. FIG. 13 is a functional block diagram depicting an equivalent model 1300 of the pipe section 1205 of FIG. 12 that the processor 110 generates. In one embodiment, the processor 110 generates this model once the pipe 140 is laid. In another embodiment, an operator of the inspection system 100, 175 transmits a command to the processor 110 to generate the model 1300 for a deformity 1210. In yet another embodiment, the processor 110 transmits an input waveform 235 along the pipe 140 and determines from the reflected component 245 that a deformity 1210 exists. In one embodiment, the processor 110 determines that a deformity 1210 exists by computing the likelihood functions on the basis of the observed data taken together with models of the various defects.

The equivalent model 1300 depicted in FIG. 13 is similar to the equivalent model 300 depicted in FIG. 3. The equivalent model 1300 of FIG. 13 includes many of the same components (e.g., the analyzer noise sources 315, the first remainder 330) as the equivalent model 300 shown in FIG. 3. In one embodiment, the analyzer 120 simulates the input waveform 235 that is transmitted along the pipe 140 as a model deformity detecting input waveform 1305. The model deformity detecting input waveform 1305 is shown at the lower left corner of FIG. 13. The analyzer 120 transmits the model deformity detecting input waveform 1305 to the wave launcher 130 in preparation for the launching of waveform 1305 along the central axis of the model section.

As shown in FIG. 13, the processor 110 uses a model length 1310 and a model thickness 1315 as portions of the model reflected component 333 to model the deformity 1210. In one embodiment, the processor 110 iteratively adjusts the model length 1310 and/or the model thickness 1315 until the total model reflected component 380, as described above with respect to FIG. 3, accurately reflects the reflected component 245 (shown in FIG. 2) of the section 1205 of the pipe 140 having the deformity 1210. In another embodiment, the processor 110 uses the method of maximum likelihood to determine the length 1115 and the thickness 1120 of the deformity 1210. Although described above as modeling and determining the length 1115 and the thickness 1120 of the deformity 1210, the processor 110 can determine any parameter of the deformity 1210 to determine the characteristics of the deformity 1210.

Figure 14:
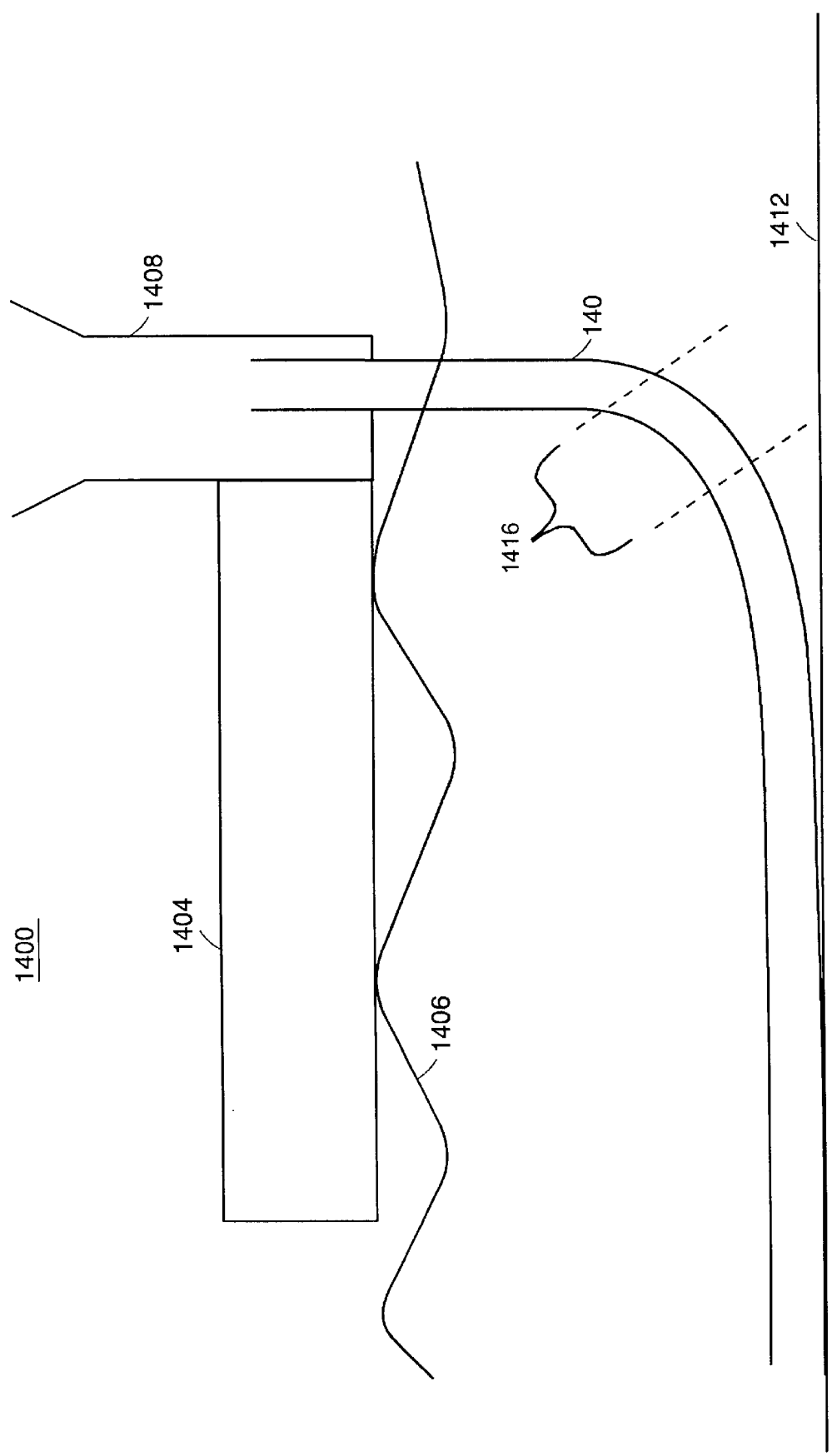
FIG. 14 is a conceptual diagram depicting an illustrative pipe being deployed.

FIG. 14 is a conceptual diagram depicting an illustrative embodiment of a system 1400 to deploy the pipe 140 of FIGS. 1A and 1B in an underwater sea bed. As briefly described above with respect to FIGS. 1A and 1B, the systems of FIGS. 1A and 1B typically operate on a barge 1404 adapted for laying pipe along a bed of a body of water 1406, such as an ocean, sea, bay, lake, river or the like. The barge 1404 is any device that can carry sections of pipe along the body of water 1406 to a particular destination.

In one embodiment, the barge 1404 transports sections (not shown) of pipe 140 and an operator of the barge 1404 moves a section of pipe 140 into a pipe laying tower 1408. In other embodiments, an electrical and/or mechanical device moves the sections of pipe into the pipe laying tower 1408. For example, a conveyor belt transports the sections of pipe into the pipe laying tower 1408. The pipe laying tower 1408 typically transforms multiple sections of pipe into a single pipe. The pipe laying tower 1408 may position the pipe vertically for entry into the body of water 1406. Alternatively, the pipe laying tower 1408 can orient the pipe horizontally. The variation in the positioning of the pipe for entry into the body of water 1406 can be for a variety of reasons, such as ease of entry into the body of water 1406, ease of transporting the pipe into the pipe laying tower 1408, and the like. In particular, the operator of the barge 1404 orients the pipe vertically for entry into the body of water 1406 when only a relatively small opening exists for insertion into the body of water 1406, such as a small gap in an ice patch.

Upon entry into the body of water 1406, the pipe 140 experiences external factors, such as water pressure, current, relative motion between the barge 1404 and the sea bed 1412, and the like. Furthermore, a section 1416 of the pipe 140 can particularly be at risk to these external forces due to its particular position along the pipe 140. In one embodiment, to alleviate such a problem, in response to information from the processor 110, 180 or 182, the operator of the barge 1404 alters the orientation of the pipe laying tower 1408. For example, an operator positions the pipe laying tower 1408 horizontally with respect to the barge 1404 rather than the vertical orientation illustrated in FIG. 14. In another embodiment, in response to information from the processor 110, 180 or 182, the barge commander moves the barge to compensate for the external forces. Another technique used to combat the effects of these external forces upon one or more sections 1416 of the pipe 140 is described below with respect to FIG. 15B.

Figure 15A:
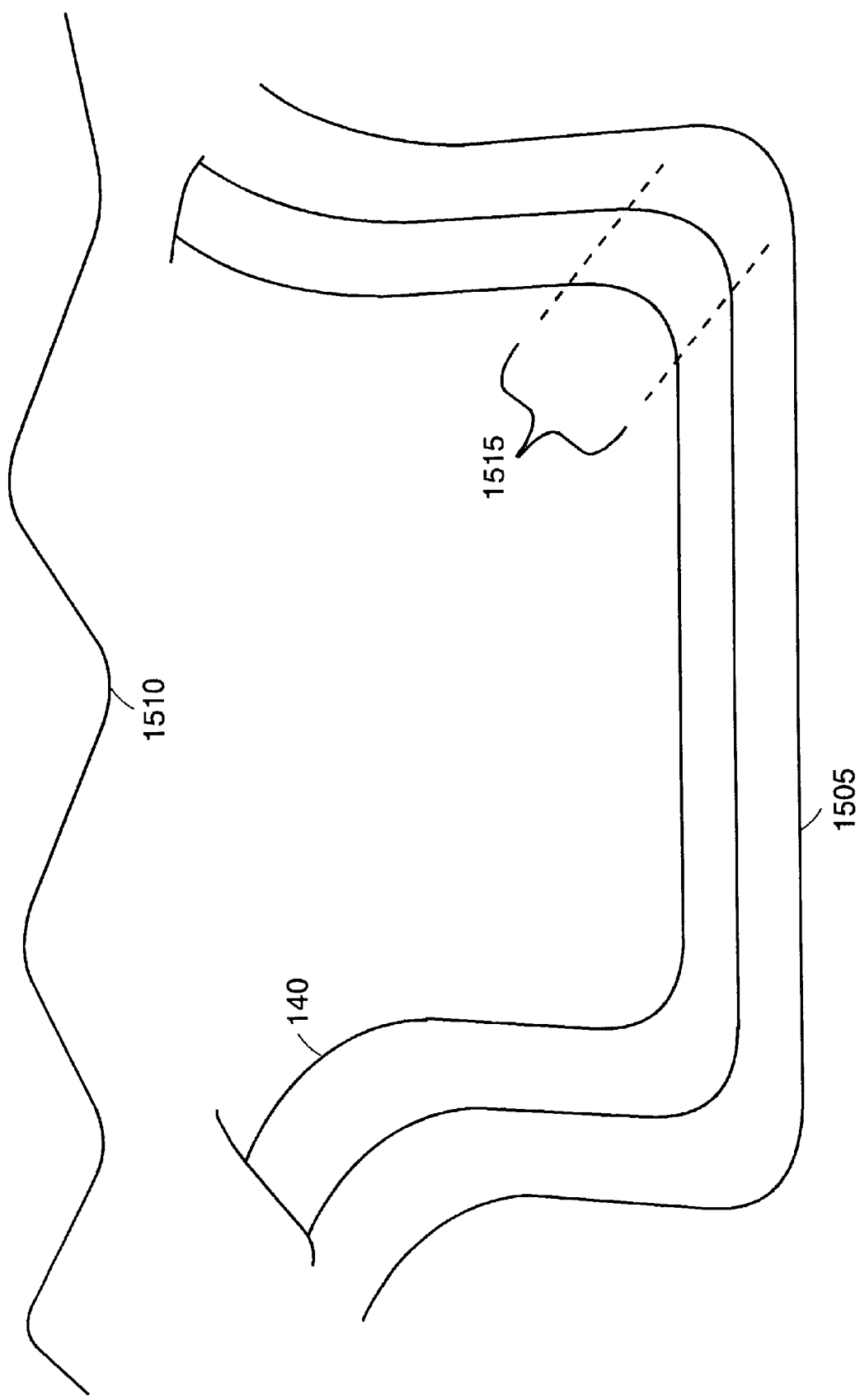
FIG. 15A depicts an illustrative deployed pipe.

FIG. 15A illustrates a deployed pipe 140. After being deployed from the pipe laying tower 1408 of the barge 1404, the pipe 140 lies along the floor 1505 of a body of water 1510, such as an ocean floor. Besides the external forces described above with respect to FIG. 14 that a pipe 140 or a section of pipe typically experiences, the temperature of the water can be another factor that affects the operation of the pipe 140. Once laid, the contents of a section 1515 of the pipe 140 can be particularly affected by these external factors associated with the external forces. For example, if a particular area in the body of water 1510 is extremely cold, the contents of a section of the pipe 140 (e.g., the contents of the section 1515) can freeze. If such freezing occurs, the frozen contents of the section 1515 affects (e.g., blocks, slows) the transmission of the contents of the rest of the pipe 140.

Likewise, if the particular section 1515 of the pipe 140 is subject to a high water pressure, the pressure can distort the section 1515 and consequently affect the flow of the transmitted fluid. In one embodiment, the operator of the inspection system 100, 175 determines possible problem areas that might be subject to extreme stresses (e.g., extreme temperatures) relative to the rest of the pipe 140. In one embodiment, the operator determines problem areas based on thermodynamic calculations using knowledge of the temperature and pressure of the pipe's environment.

In one embodiment, a pipe manufacturer constructs the section 1515 of the pipe 140 using a different material than the rest of the pipe 140. For example, a pipe manufacturer constructs most of the pipe 140 using steel while the pipe manufacturer constructs the section 1515 with another material that more aptly handles the stresses, strains, and pressure compared to steel, such as, but not limited to, graphite or kevlar. Additional replacements to more than one section of the pipe 140 typically occur when there are multiple sections of the pipe 140 that experience problems with stresses, strains, and pressures relative to the rest of the pipe 140.

Figure 15B:
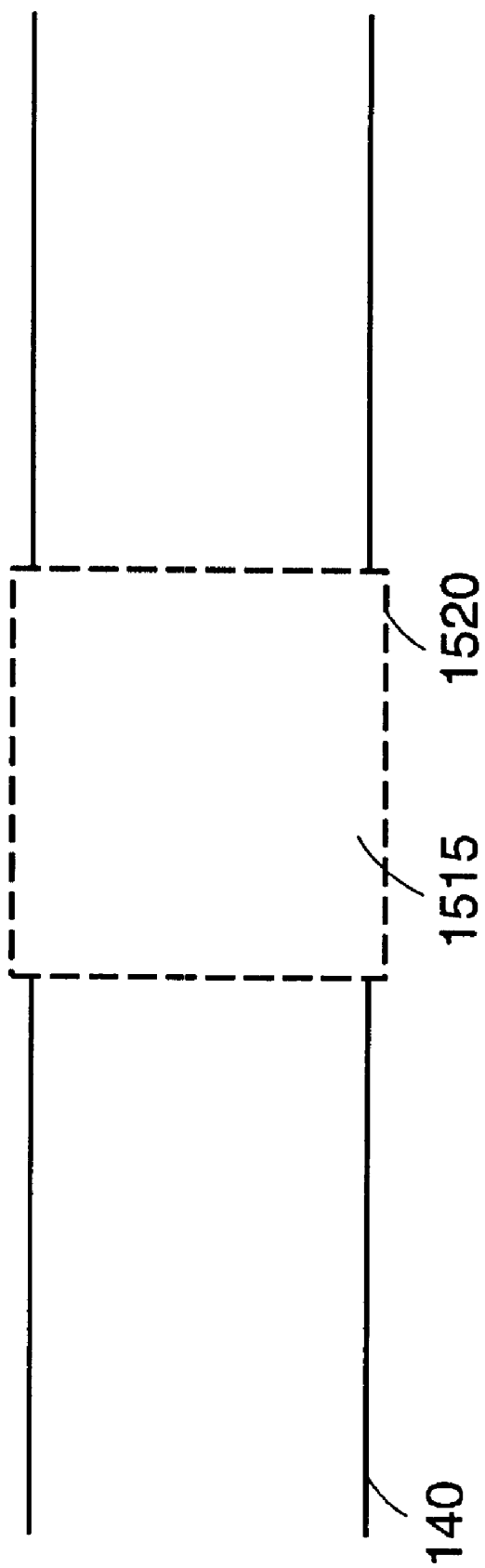
FIG. 15B is a conceptual diagram depicting an illustrative method for defrosting an anomaly in a section of the pipe of FIG. 15A.

FIG. 15B illustrates an approach to defrosting a frozen blockage (not shown), such as an anomaly 150, located in a section 1515 of the pipe 140. An operator of the inspection system 100, 175 coats the section 1515 of the pipe 140 with a microwave-sensitive wrap 1520. The operator then transmits a command to the analyzer 120 (e.g., via the keyboard 180b) to generate a microwave waveform for transmission into the pipe 140. After the generation of the microwave waveform, the analyzer 120 transmits the microwave waveform to the wave launcher 130 and the wave launcher 130 transmits the microwave waveform along the pipe 140. When encountering the microwave-sensitive wrap 1520 of the section 1515, the microwave waveform heats the wrap 1520 to defrost the blockage 1515.

Although the microwave-sensitive wrap typically helps in the efficiency of defrosting the contents of a section 1515, in another embodiment the operator transmits the microwave waveform along the pipe 140 having frozen contents in a section 1515 not covered by a wrap 1520. The efficiency of the defrosting of the frozen contents in the section 1515 depends on several factors, such as the material that the section 1515 is made from and the heat transfer characteristics of the material in response to a microwave waveform.

Rather than a microwave-sensitive wrap 1520, the operator could also cover the section 1515 with a microwave-sensitive coating. Similar to the effect that a microwave waveform has on the wrap 1520 described above, a microwave waveform invokes an increase in the temperature of the microwave-sensitive coating (and the section 1515) to defrost the contents of the section 1515.

As mentioned above, an operator of the inspection system 100, 175 can use the system 100, 175 to inspect the pipe 140 prior to laying the pipe 140 at its final location (e.g., a body of water). An operator can perform this inspection as a quality control measurement. For example, the operator can inspect the pipe 140 for an anomaly 150 that arose during manufacture or transportation of the pipe 140, or for an anomaly 150 that arose due to the age of the pipe 140, such as rust. If the inspection system 100, 175 detects an anomaly early enough, the operator using the inspection system 100, 175 may decide not to use a particular section of pipe 140 because of an anomaly 150, thus saving future costs that the operator would endure to retrieve the pipe 140 to remove the defective section.

The pipe inspection system of the invention may be embodied in other specific forms without departing from the spirit or essential characteristics of the claimed invention. By way of example, various components depicted as individual modules may be integrated into a single module, and various electronic devices employed with the invention may be embodied in software, microcode or object code. Moreover, the cross-sectional shape of the pipe need not be circular, nor does the wave transmitted through the pipe need to be transmitted along a central longitudinal axis. The foregoing embodiments are therefore to be considered in all respects illustrative rather than limiting on the present invention.

What is claimed is:

1. A pipe inspection system comprising,
    a wave launcher in communication with a pipe and adapted to transmit an input waveform having a selected input energy along a longitudinal axis of said pipe, and to receive a reflected portion of said input waveform from said pipe, said reflected portion having a characteristic reflected energy,
    an analyzer in communication with said waver launcher and adapted to generate said input waveform, and to receive said reflected portion of said input waveform from said wave launcher, and
    a processor in communication with said analyzer and adapted to process said input waveform with said reflected portion and a modeled reflected waveform to determine a characteristic of said pipe.

2. The system of claim 1, wherein said launcher is further adapted to transmit said input waveform with a selected cutoff frequency.

3. The system of claim 1, wherein said characteristic is a quality control measurement made prior to laying said pipe.

4. The system of claim 1, wherein said processor is further adapted to process said input waveform with said reflected portion and said modeled reflected waveform to determine an axial curvature of a section of said pipe as said pipe is being laid.

5. The system of claim 4, wherein said section of said pipe extends from an above water location to an underwater location.

6. The system of claim 4 further adapted to repeat determination of said curvature a plurality of times to enable said processor to provide a substantially real-time measurement of said curvature.

7. The system of claim 6 further comprising a display adapted to display a graphical representation of said substantially real-time measurement of said curvature of said section of said pipe to a user.

8. The system of claim 4, wherein said processor is further adapted to process said input waveform with said reflected portion and said modeled reflected waveform to determine an axial curvature of a plurality of subsections of said section of said pipe, and to combine said axial curvatures of said subsections to determine said axial curvature of said section of said pipe.

9. The system of claim 1, wherein said launcher is further adapted to transmit said input waveform with a selected mode.

10. The system of claim 9, wherein said selected mode is $TE_{11}$.

11. The system of claim 9, wherein said selected mode is other than $TE_{11}$, and said processor is adapted to process a $TE_{11}$ modal component of said reflected portion along with one or more other modal components of said reflected portion to determine an axial curvature of a section of said pipe.

12. The system of claim 11, wherein said processor is further adapted to process a distribution of energy between said $TE_{11}$ modal component of said reflected portion and said one or more other modal components of said reflected portion to determine said axial curvature of said section of said pipe.

13. The system of claim 4, wherein said processor is further adapted to process said input waveform with said reflected portion to determine a diameter at a location along said pipe as said pipe is being laid.

14. The system of claim 4, wherein said processor is further adapted to process said input waveform with said reflected portion to determine a diameter at a location along said pipe as said pipe is being laid.

15. The system of claim 4, wherein said processor is further adapted to process said input waveform with said reflected portion to determine a plurality of diameters, each at one of a plurality of locations along said pipe as said pipe is being laid.

16. The system of claim 15, wherein said processor is further adapted to process said axial curvature with said plurality of diameters to determine a three-dimensional representation of said section of said pipe as said pipe is being laid.

17. The system of claim 1, wherein said characteristic is an anomaly in said pipe and said wave launcher is further adapted to transmit a microwave waveform into said pipe to dissolve said anomaly.

18. The system of claim 17 further comprising a microwave sensitive coating on a portion of said pipe and adapted to heat in response to said microwave waveform to melt said anomaly.

19. The system of claim 17 further comprising a microwave responsive wrap on a portion of said pipe and adapted to heat in response to said microwave waveform to melt said anomaly.

20. The system of claim 17, wherein said pipe includes a portion, adapted to heat in response to said microwave waveform to melt said anomaly.

21. The system of claim 20, wherein said portion is located in a section of said pipe susceptible to said anomalies.

22. The system of claim 1, wherein at least one of said wave launcher, said analyzer, and said processor are located inside said pipe.

23. A pipe inspection system comprising,
    a wave launcher adapted to transmit an input waveform having a selected input energy along a longitudinal axis of a first section of pipe, and to receive a reflected portion of said input waveform from said pipe, said reflected portion having a characteristic reflected energy,
    an analyzer in communication with said waver launcher and adapted to generate said input waveform, and to receive said reflected portion of said input waveform from said wave launcher,
    a clamp in mechanical communication with said analyzer, said clamp adapted to temporarily connect said first section of said pipe with a second section of said pipe, an umbilical adapted to move at least one of said wave launcher and said analyzer from said first section of pipe to said second section of pipe to enable said wave launcher to transmit said input waveform along said longitudinal axis of said first section of said pipe and said second section of said pipe.

24. The system of claim 23, wherein said clamp further comprises a connector adapted to mate with said umbilical.

25. The system of claim 24, wherein an end of said umbilical is keyed to mate with said connector.

26. The system of claim 23, wherein said clamp further comprises at least one of mechanical means, grappling means, frictional means, electrical means, suction, and magnetic means.

27. The system of claim 23, wherein said umbilical is made from at least one of plastic, rubber, fiber, and rope.

28. A method for inspecting a pipe comprising the steps of:

positioning a wave launcher inside a first section of said pipe, positioning an analyzer inside said first section of said pipe, said analyzer in communication with said wave launcher, positioning a second section of said pipe a particular distance away from a location of said first section of said pipe, temporarily connecting said first section of said pipe with said second section of said pipe with a clamp;

actuating an umbilical to move at least one of said wave launcher and said analyzer from said first section of said pipe to said second section of said pipe to enable said wave launcher to transmit an input waveform along a longitudinal axis of said first section of said pipe and said second section of said pipe to inspect said pipe; and welding said first section of said pipe with said second section of said pipe.

* * * * *

UNITED STATES PATENT AND TRADEMARK OFFICE
CERTIFICATE OF CORRECTION

PATENT NO.      : 6,597,997 B2
DATED           : July 22, 2003
INVENTOR(S)     : Tingley It is certified that error appears in the above-identified patent and that said Letters Patent is hereby corrected as shown below:

Column 31,
Line 29, replace "waver" with -- wave --.

Column 32,
Line 61, replace "waver" with -- wave --.

Signed and Sealed this

Ninth Day of December, 2003

JAMES E. ROGAN
*Director of the United States Patent and Trademark Office*